United States Patent
Saito et al.

(10) Patent No.: US 9,913,580 B2
(45) Date of Patent: Mar. 13, 2018

(54) APPARATUS, METHOD, AND NON-TRANSITORY MEDIUM FOR OPTICAL STABILIZATION AND DIGITAL IMAGE REGISTRATION IN SCANNING LIGHT OPHTHALMOSCOPY

(71) Applicants: CANON KABUSHIKI KAISHA, Tokyo (JP); UNIVERSITY OF ROCHESTER, Rochester, NY (US)

(72) Inventors: Kenichi Saito, Pittsford, NY (US); Qiang Yang, Rochester, NY (US); Jie Zhang, Pittsford, NY (US); Koji Nozato, Rochester, NY (US)

(73) Assignees: Canon Kabushiki Kaisha, Tokyo (JP); University of Rochester, Rochester, NY (US)

( * ) Notice: Subject to any disclaimer, the term of this patent is extended or adjusted under 35 U.S.C. 154(b) by 308 days.

(21) Appl. No.: 14/490,449

(22) Filed: Sep. 18, 2014

(65) Prior Publication Data
US 2015/0077710 A1 Mar. 19, 2015

Related U.S. Application Data

(60) Provisional application No. 61/880,057, filed on Sep. 19, 2013, provisional application No. 61/886,507, (Continued)

(51) Int. Cl.
*G06K 9/00* (2006.01)
*A61B 3/10* (2006.01)
(Continued)

(52) U.S. Cl.
CPC .......... *A61B 3/1025* (2013.01); *A61B 3/0025* (2013.01); *A61B 3/12* (2013.01);
(Continued)

(58) Field of Classification Search
None
See application file for complete search history.

(56) References Cited

U.S. PATENT DOCUMENTS

| 7,198,367 B2 | 4/2007 | Akita et al. |
| 7,980,696 B1 | 7/2011 | Taki et al. |
| (Continued) | | |

FOREIGN PATENT DOCUMENTS

| EP | 2633802 A1 | 9/2013 |
| WO | 2006/105903 A2 | 10/2006 |

OTHER PUBLICATIONS

David W. Arathorn, Qiang Yang, Curtis R. Vogel, Yuhua Zhang, Pavan. Tiruveedhula, Austin Roorda, Retinally Stabilized Cone-Targeted Stimulus Delivery, Optics Express, Oct. 17, 2007, 15(21):13731-13744, Optical Society of America, Washington DC, 2007.

(Continued)

*Primary Examiner* — Weiwen Yang
(74) *Attorney, Agent, or Firm* — Canon U.S.A., Inc. IP Division

(57) ABSTRACT

Apparatus, method, and non-transitory medium for optical stabilization and digital image registration in scanning light ophthalmoscopy. Scanning an object with measurement light. Acquire an image of the object to be examined based on return light from the object. Acquire information which indicates movement of the object to be examined based on a plurality of acquired images. Control the scanning based on the information which indicates the movement of the object to be examined. Performing registration of the plurality of images.

10 Claims, 11 Drawing Sheets

Related U.S. Application Data filed on Oct. 3, 2013, provisional application No. 61/913,177, filed on Dec. 6, 2013, provisional application No. 61/930,794, filed on Jan. 23, 2014.

(51) Int. Cl.
*A61B 3/12* (2006.01)
*A61B 3/14* (2006.01)
*A61B 3/00* (2006.01)
*G06T 7/246* (2017.01)

(52) U.S. Cl.
CPC ............... *A61B 3/14* (2013.01); *G06T 7/246* (2017.01); *G06T 2207/10016* (2013.01); *G06T 2207/30041* (2013.01)

(56) References Cited

U.S. PATENT DOCUMENTS

| | | | |
|---|---|---|---|
| 8,201,943 B2 | 6/2012 | Hammer et al. | |
| 8,238,012 B2 | 8/2012 | Kobayashi | |
| 8,444,268 B2 | 5/2013 | Hammer et al. | |
| 8,534,835 B2 | 9/2013 | Murata et al. | |
| 8,593,514 B2 | 11/2013 | Satake | |
| 2003/0160942 A1* | 8/2003 | Xie | A61B 3/102 351/205 |
| 2007/0013918 A1* | 1/2007 | Hauger | A61B 3/1005 356/512 |
| 2007/0216909 A1 | 9/2007 | Everett et al. | |
| 2008/0100612 A1 | 5/2008 | Dastmalchi et al. | |
| 2012/0002164 A1 | 1/2012 | Yamamoto et al. | |
| 2012/0147326 A1 | 6/2012 | Yatagai et al. | |
| 2012/0268717 A1* | 10/2012 | Zhou | A61B 3/1015 351/221 |
| 2013/0011035 A1 | 1/2013 | Shimoyama et al. | |
| 2013/0141695 A1 | 6/2013 | Buckland et al. | |
| 2013/0169931 A1 | 7/2013 | Lee et al. | |
| 2013/0194581 A1 | 8/2013 | Yoshida | |
| 2014/0111767 A1 | 4/2014 | Murase | |

OTHER PUBLICATIONS

David W. Arathorn, Scott B. Stevenson, Qiang Yang, Pavan Tiruveedhula, Austin Roorda, How the Unstable Eye Sees a Stable and Moving World, Journal of Vision, Aug. 29, 2013, 13(10),22 1-19, The Association for Research in Vision and Ophthalmology, Rockville, MD, 2013.

Boy Braaf, Kari V. Vienola, Christy K. Sheehy, Qiang Yang, Koenraad A. Vermeer, Pavan Tiruveedhula, David W. Arathorn, Austin Roorda, Real-Time Eye Motion Correction in Phase-Resolved OCT Angiography With Tracking SLO, Biomedical Optics Express, Dec. 11, 2012, 4(1):51-65, Optical Society of America, Washington DC, 2007.

David H. Brainard, The Psychophysics Toolbox, Sep. 2000, UC Santa Barbara, Santa Barbara, CA, 2000.

Stephen A. Burns, Remy Tumbar, Ann E. Elsner, Daniel Ferguson, and Daniel X. Hammer, Large-Field-of-View, Modular, Stabilized, Adaptive-Optics-Based Scanning Laser Ophthalmoscope, Journal of Optical Society of America A, Apr. 11, 2007, 24(5):1313-1326, Optical Society of America, Washington DC, 2007.

T. N. Cornsweet, H. D. Crane, Accurate Two-Dimensional Eye Tracker Using First and Fourth Purkinje Images, of Optical Society of America, Aug. 1973, 63(8):921-928, Journal Optical Society of America, Washington DC, 1973.

Hewitt D. Crane, Carroll M. Steele, Generation-V Dual-Purkinje-Image Eyetracker, Applied Optics, Feb. 15, 1985, 24(4)527-537, Optical Society of America, Washington DC, 1985.

Raymond Dodge, Thomas Sparks Cline, The Angle Velocity of Eye Movements, Psychological Review, Mar. 8, 1901, 8(2):145-157, The Macmillan Company, Lancaster, PA, 1901.

Alfredo Dubra, Zachary Harvey, Registration of 2D Images from Fast Scanning Ophthalmic Instruments, Proceedings of 4th International Workshop, WBIR 2010, Lübeck, Germany, Biomedical Image Registration, Lecture Notes in Computer Science Jul. 11-13, 2010, 6204:60-71, Springer-Verlag Berlin Heidelberg, Berlin DE, 2010.

Alfredo Dubra, Yusufu Sulai, Reflective Afocal Broadband Adaptive Optics Scanning Ophthalmoscope, Biomedical Optics Express, Mar. 27, 2011, 2(6):1757-1768, Optical Society of America, Washington DC, 2011.

R. Daniel Ferguson, Daniel X. Hammer, Chad E. Bigelow, Nicusor V. Iftimia, Teoman E. Ustun, Stephen A. Burns, Ann E. Elsner, David R. Williams, Tracking Adaptive Optics Scanning Laser Ophthalmoscope, Oct. 2009.

R. Daniel Ferguson, Zhangyi Zhong, Daniel X. Hammer, Mircea Mujat, Ankit H. Patel, Cong Deng, Weiyao Zou, Stephen A. Burns, Adaptive Optics Scanning Laser Ophthalmoscope with Integrated Wide-Field Retinal Imaging and Tracking, Author Manuscript, PubMed Central, May 1, 2011, U.S. National Library of Medicine, Bethesda MD, 2011.

Manuel Guizar-Sicairos, Samuel T. Thurman, James R. Fienup, Efficient Subpixel Image Registration Algorithms, Optics Letters, Jan. 15, 2008, 33(2):156-158, Optical Society of America, Washington DC, 2008.

Daniel X. Hammer, R. Daniel Ferguson, Chad E. Bigelow, Nicusor V. Iftimia, Teoman E. Ustun, Stephen A. Burns, Adaptive Optics Scanning Laser Ophthalmoscope for Stabilized Retinal Imaging, Optics Express, Apr. 17, 2006, 14(8):3354-3367, Optical Society of America, Washington DC, 2006.

Wolf M. Harmening, William S. Tuten, Austin Roorda, Lawrence C. Sincich, Mapping the Perceptual Grain of the Human Retina, The Journal of Neuroscience, Apr. 16, 2014, 34(16):5667-5677, The Society for Neuroscience, Washington DC, 2014.

Robert Michael Jones, U. Tulunay-Keesey, Accuracy of Image Stabilization by an Optical-Electronic Feedback System, Vision Research, Jan. 1975, 15(1):57-61, Pergamon Press, Oxford, GB, 1975.

Mario Kleiner, David Brainard, Denis Pelli, Allen Ingling, Richard Murray, Christopher Broussard, Frans Cornelissen, What's New in Psychtoolbox-3?, A Free Cross-Platform Toolkit for Psychophysics With Matlab & GNU/Octave, Sep. 21, 2007.

Junzhong Liang, David R. Williams, Donald T. Miller, Supernormal Vision and High-Resolution Retinal Imaging Through Adaptive Optics, Journal of Optical Society of America A, Nov. 1997, 14(11):2884-2892, Optical Society of America, Washington DC, 1997.

Susana Martinez-Conde, Stephen L. Macknik, David H. Hubel, The Role of Fixational Eye Movements in Visual Perception, Nature Reviews Neuroscience, Mar. 2004, 5(3):229-240, Nature Publishing Group., London, UK, 2004.

Jeffery B. Mulligan, Recovery of Motion Parameters from Distortions in Scanned Images, Nov. 20-21, 1997.

Jacob Nachmias, Two-Dimensional Motion of the Retinal Image during Monocular Fixation, Journal of Optical Society of America, Sep. 1959, 49(9):901-908, Optical Society of America, Washington DC, 1959.

Dietmar Ott, Wolfgang J. Daunicht, Eye Movement Measurement with the Scanning Laser Ophthalmoscope, Clinical Vision Sciences, 1992, 7(6):551-556, Pergamon Press Ltd., Oxford, GB, 1992.

Denis G. Pelli, The VideoToolbox Software for Visual Psychophysics: Transforming Numbers into Movies, Spatial Vision, 1997, 10(4):437-442, Brill, Boston, MA, 1997.

Lorrin A. Riggs, Floyd Ratliff, Janet C. Cornsweet, Tom N. Cornsweet, The Disappearance of Steadily Fixated Visual Test Objects, Journal of Optical Society of America, Jun. 1953, 43(6):495-501, Optical Society of America, Washington DC, 1953.

Lorrin A. Riggs, John C. Armington, Floyd Ratliff, Motions of the Retinal Image during Fixation, Journal of Optical Society of America, Apr., 1954, 44(4):315-321, Optical Society of America, Washington DC, 1954.

(56) References Cited

OTHER PUBLICATIONS

L. A. Riggs, A. M. L. Schick, Accuracy of Retinal Image Stabilization Achieved With a Plane Mirror on a Tightly Fitting Contact Lens, Vision Research, Feb. 1968, 8(2):159-169, Pergamon Press, Oxford, GB, 1968.

Austin Roorda, Fernando Romero-Borja, William J. Donnelly III, Hope Queener, Adaptive Optics Scanning Laser Ophthalmoscopy, Optics Express, May 6, 2002, 10(9):405-412, Optical Society of America, Washington DC, 2002.

Ethan A. Rossi, Piero Rangel-Fonseca, Keith Parkins, William Fischer, Lisa R. Latchney, Margaret A. Folwell, David R. Williams, Alfredo Dubra, Mina M. Chung, In Vivo Imaging of Retinal Pigment Epithelium Cells in Age Related Macular Degeneration, Biomedical Optics Express, Oct. 18, 2013, 4(11):2527-2539, Optical Society of America, Washington DC, 2013.

S-334 Miniature Piezo Tip/Tilt-Mirror, Data Sheet, May 11, 2011, Physik Instrumente GmbH & Co, Karlsruhe, DE, 2011.

Fabrizio Santini, Gabriel Redner, Ramon Iovin, Michele Ruccif, EyeRIS: A General-Purpose System for Eye-Movement-Contingent Display Control, Behavior Research Methods, Aug. 2007, 39(3):350-364, Psychonomic Society, Inc., Madison, WI, 2007.

Christy K. Sheehy, Qiang Yang, David W. Arathorn, Pavan Tiruveedhula, Johannes F. de Boer, Austin Roorda, High-Speed, Image-Based Eye Tracking With a Scanning Laser Ophthalmoscope, Biomedical Optics Express, Oct. 1, 2012, 3(10):2611-2622, Optical Society of America, Washington DC, 2012.

Lawrence C. Sincich, Yuhua Zhang, Pavan Tiruveedhula, Jonathan C. Horton. Austin Roorda, Resolving Single Cone Inputs to Visual Receptive Fields, Nature Neuroscience, Aug. 2009, 12(8):967-969, Nature Publishing Group., London, UK, 2009.

Martin Stetter, Raimund A. Sendtner, George T. Timberlake, A Novel Method for Measuring Saccade Profiles Using the Scanning Laser Ophthalmoscope, Vision Research, Jul. 1996, 36(13):1987-1994, Elsevier Science Ltd., Amsterdam, NL, 1996.

Scott B. Stevenson, Austin Roorda, Correcting for Miniature Eye Movements in High Resolution Scanning Laser Ophthalmoscopy, Ophthalmic Technologies XV, Proceedings of SPIE, Apr. 18, 2005, vol. 5688, pp. 145-151, SPIE, Bellingham, WA, 2005.

Kari V. Vienola, Boy Braaf, Christy K. Sheehy, Qiang Yang, Pavan Tiruveedhula, David W. Arathorn, Johannes F. de Boer, Austin Roorda, Real-Time Eye Motion Compensation for OCT Imaging With Tracking SLO, Biomedical Optics Express, Nov. 1, 2012, 3(11):2950-2963, Optical Society of America, Washington DC, 2012.

Curtis R. Vogel, David W. Arathorn, Austin Roorda, Albert Parker, Retinal Motion Estimation in Adaptive Optics Scanning Laser Ophthalmoscopy, Optics Express, Jan. 23, 2006, 14(2):487-497, Optical Society of America, Washington DC, 2006.

Qiang Yang, David W. Arathorn, Pavan Tiruveedhula, Curtis R. Vogel, Austin Roorda, Design of an Integrated Hardware Interface for AOSLO Image Capture and Cone-Targeted Stimulus Delivery, Optics Express, Aug. 16, 2010, 18(7):17841-17858, Optical Society of America, Washington DC, 2010.

Qiang Yang, Jie Zhang, Koji Nozato, Kenichi Saito, David R. Williams, Austin Roorda, Ethan A. Rossi, Closed-Loop Optical Stabilization and Digital Image Registration in Adaptive Optics Scanning Light Ophthalmoscopy, Biomedical Optics Express, Aug. 26, 2014, 5(9):3175-3191, Optical Society of America, Washington DC, 2014.

* cited by examiner

APPARATUS, METHOD, AND NON-TRANSITORY MEDIUM FOR OPTICAL STABILIZATION AND DIGITAL IMAGE REGISTRATION IN SCANNING LIGHT OPHTHALMOSCOPY

CROSS-REFERENCE TO RELATED APPLICATIONS

This application claims the benefit of U.S. Provisional Application No. 61/880,057, filed Sep. 19, 2013, U.S. Provisional Application No. 61/886,507, filed Oct. 3, 2013, U.S. Provisional Application No. 61/913,177, filed Dec. 6, 2013, and U.S. Provisional Application No. 61/930,794, filed Jan. 23, 2014. U.S. Provisional Application Nos. 61/880,057, 61/886,507, 61/913,177, and 61/930,794 are incorporated by reference in their entirety.

STATEMENT REGARDING FEDERALLY SPONSORED RESEARCH OR DEVELOPMENT

This invention was made with government support under grant numbers EY014375 and EY001319 awarded by the National Institutes of Health. The Government has certain rights in this invention.

BACKGROUND

Field of Art

The present disclosure relates to optical stabilization in scanning imaging system and systems, methods, and non-transitory computer readable medium with instructions for controlling the optical stabilization.

Description of the Related Art

The scanning light ophthalmoscope (SLO) has become an important tool for the study of the human retina in both normal and diseased eyes. For retinal imaging systems such as a SLO, eye movement is a big issue for imaging. The human eye is constantly in motion; even during careful fixation, normal, involuntary, microscopic eye movements, cause the scanned field of the SLO to move continuously across the retina in a constrained pattern. Fixational eye motion causes unique distortions in each SLO frame due to the slow frame rate of the SLO relative to the motion of the eye. In the normal eye, these movements tend to be rather small in amplitude. However, in patients with retinal disease or poor vision, fixational eye movements can be amplified and introduce distortions that are a major hindrance to efficient SLO imaging, in some cases precluding imaging altogether. Unfortunately, these patients are potentially some of the most interesting to study using this technology. It is therefore desirable, particularly for clinical imaging, to minimize or eliminate this motion altogether.

Many state-of-the-art SLOB suffer from two major limitations: small field of view (FOV) and a reliance on patient fixation for targeting a retinal location. Usually an SLO takes multiple images for averaging and constructing panoramic images. For constructing these images, each frame should be at an exact position. This is very difficult because the eye moves continuously during imaging. Especially, in small FOV systems such as an Adaptive Optics SLO (AO-SLO) eye movement can be quite large when compared with the frame size and sometimes the imaging area can go out of frame easily due to the eye movement.

AO-SLO has become widely used to obtain high spatial resolution images from the living human eye. However, normal, involuntary eye movements, even during careful fixation, cause the imaging field to move continuously across the retina in a constrained pattern. Normal fixational eye movements consist of drifts, tremor, and microsaccades. These motions can cause unique distortions in each AO-SLO video frame due to the relatively slow frame rate of AO-SLO. The frame rate of the AO-SLO is set by the scan velocity of the slow scanning mirror and the velocity of the fast scanning mirror.

The velocity of the fast scanning mirror in the AO-SLO is the primary limitation to achieving very high frame rates that would effectively eliminate image distortion within individual frames. The frame rate of the AO-SLOs is limited by the speed of appropriately-sized, fast scanning mirrors, which achieve a maximum frequency of ~16 kHz. Uses of these fast scanning mirrors require that the AO-SLO image be de-warped (to remove sinusoidal distortions induced from the fast resonant scanner), registered (to facilitate averaging), and averaged (to increase SNR) to generate an image for qualitative or quantitative analysis. Image registration works by recovering the eye motion and nullifying it, and is required to generate high SNR images from AO-SLO image sequences.

In the past, photographic techniques were first used to measure eye movements. One of the earliest attempts to precisely measure the two dimensional motion of the retinal image employed the 'optical-lever' method, a technique that measured the light reflected from a plane mirror attached to the eye with a tightly fitting contact lens. The optical lever method was used to both measure eye movements and deliver stabilized stimuli to the retina; this method has achieved very precise optical stabilization, with an error rate of 0.2-0.38 arcminutes, or less than the diameter of a foveal cone (~0.5 arcminutes). Despite the precision of optical lever method, the invasive nature of this method and its limitations for stimulus delivery limits it usefulness and has been largely replaced with dual-Purkinje image (dPi) eye trackers. The dPi eye trackers use the Purkinje images (i.e. images of a light source reflected from the cornea and lens) to non-invasively measure eye position. The dPi eye trackers measure eye motion and manipulate visual stimuli with a precision of ~1 arcminute. Each of these methods indirectly infer the motion of the retinal image.

One solution to the problem of imaging live retinas is to use post-processing which can cause a long delay in delivering the video or require large amounts of processing power. Most clinical and experimental uses of the instrument require that the raw AO-SLO image be de-warped and stabilized to present the user with an interpretable image. Another solution to this problem is an eye position tracking system. Prior art eye position tracking systems used mostly open loop control algorithms. These eye tracking systems detect eye position using a position detection apparatus and shift the imaging area according to the eye movement using tracking mirrors. Image based position calculation methods including methods which detect specific features can be used in the position detection apparatus. In addition, two scanning mirrors are used as tracking mirrors.

Implementing an eye position tracking system raises the cost of the overall system. Two galvano scanners are needed as tracking mirrors in addition to the resonant scanner and the galvano scanner. In addition, each tracking mirror should be conjugate with the pupil or the eye rotation center. These additions add to the complexity of the optical system and increase costs. The following disclosure is directed towards providing a better solution to this problem. The following

SUMMARY

In one embodiment, an image acquisition apparatus comprises: a scanning unit configured to scan an object to be examined with a measurement light; a first acquisition unit configured to acquire an image of the object to be examined based on return light from the object to be examined, to which the measurement light is irradiated; a second acquisition unit configured to acquire information which indicates movement of the object to be examined based on a plurality of images acquired by the first acquisition unit; a control unit configured to control the scanning unit based on the information which indicates the movement of the object to be examined; and a registration unit configured to perform registration of the plurality of images acquired by the first acquisition unit, the plurality of images including an image of the object to be examined acquired by the first acquisition unit based on the return light from the object to be examined of the measurement light which is scanned by the scanning unit controlled by the controlling unit.

In an alternative embodiment, the registration unit performs the registration based on the information indicating the movement which is used by the control unit.

In an alternative embodiment, the scanning unit includes: a first scanning unit which scans the object to be examined with the measurement light in a first direction and a second scanning unit which scans the object to be examined with the measurement light in a second direction different from the first direction at a slower speed than the first scanning unit and the control unit controls the second scanning unit without controlling the first scanning unit based on the information indicating the movement.

In an alternative embodiment, the registration unit performs the registration based on the information indicating the movement of the object to be examined in the first direction, which is included in the information indicating the movement for the object to be examined.

In an alternative embodiment, the registration unit performs the registration in the second direction based on the information indicating the movement of the object to be examined in the second direction, which is included in the information indicating the movement of the object to be examined.

In an alternative embodiment, the first scanning unit is a resonance scanner, and the second scanning unit is a Galvano Scanner.

In an alternative embodiment, the second scanning unit is a tip/tilt scanner that scans the object to be examined with the measurement light in two orthogonal directions.

In an alternative embodiment, the scanning unit further includes a third scanning unit with a scanning speed that is slower than the first scanning unit which scans the object to be examined with the measurement light in the first direction; and the control unit controls the second scanning unit and the third scanning unit without controlling the first scanning unit based on the information indicating the movement.

In an alternative embodiment, the first scanning unit is a resonance scanner, and the second scanning unit and the third scanning unit are Galvano Scanners.

In an alternative embodiment, the image in a frame of the object to be examined, which is acquired by the first acquisition unit, is divided into a plurality of partial images; and the second acquisition unit acquires the information indicating the movement of the object to be examined based on the partial image included in a first frame and the partial image included in the second frame which is different from the first frame.

In an alternative embodiment, the first frame and the second frame are the images sequentially acquired by the first acquisition unit.

In an alternative embodiment, the second acquisition unit acquires the information indicating the movement of the object to be examined based on the a plurality of images which is acquired by applying a filter to the plurality of images acquired by the first acquisition unit.

In an alternative embodiment, the filter is a Gaussian filter.

In an alternative embodiment, the filter includes a Gaussian filter and a Sobel filter; and the second acquisition unit applies the Sobel filter to a plurality of images which are acquired by applying the Gaussian filter to a plurality of images acquired by the first acquisition unit.

In an alternative embodiment, the plurality of images acquired by the first acquisition unit includes an image of the object to be examined acquired by the first acquisition unit based on the return light from the object to be examined from the measurement light which is scanned by a scanner which is a part of the scanning unit not controlled by the control unit.

An alternative embodiment, is a method comprising: providing a light from a light source; a fast scanning step of scanning the light in a first direction by a first scanner to produce a first scanning line of light; a slow scanning step of scanning the scanning line of light in a second direction by a second scanner, wherein the second direction is substantially orthogonal to the first direction to produce a first scanning area, wherein a scanning rate of the slow scanning step is slower than a scanning rate of the fast scanning step; an image constructing step of constructing an image with light from the first scanning area of the subject; a position detecting step of detecting a relative change in a position of the first scanning area on the subject by analyzing the constructed image; controlling the first scanning area of the second scanner in the second direction according to the detected relative change in the position of the first scanning area; constructing a final image by adjusting a position of the image using the relative change in the position of the first scanning area.

In an alternative embodiment, controlling the first scanning area further comprises adjusting the second scanner in two orthogonal directions according to the detected relative change in the position of the first scanning area.

In an alternative embodiment, controlling an optical tracking system for adjusting the first scanning area in the first scanning direction according to the detected relative change in the position of the first scanning area.

In an alternative embodiment, obtaining a wide image of the subject that includes the area of the subject; and wherein the wide image is used to detect the relative change in the position of the first scanning area.

In an alternative embodiment, analyzing the constructed image includes calculating a cross-correlation between a reference image and a target image to detect the relative change in the position of the first scanning area on the subject.

In an alternative embodiment, the relative change in the position of the first scanning area is decomposed into a first relative change in the first direction and a second relative change in the second direction; the first relative change in the first direction is compensated for by adjusting the position of the image along an axis in the first direction when constructing the final image; and the second relative change in the second direction is compensated for by controlling the first scanning area of the second scanner in the second direction according to the second relative change.

In an alternative embodiment, the second relative change in the second direction is also compensated for by adjusting the position of the image along an axis in the second direction when constructing the final image.

In an alternative embodiment, the final image is one of a video image or an averaged image.

In an alternative embodiment, the relative change in the position of the first scanning area is decomposed into a first relative change in the first direction and a second relative change in the second direction; and the second relative change in the second direction is compensated for by controlling the first scanning area of the second scanner in the second direction according to the second relative change and in the first direction according to the first relative change.

An alternative embodiment, is a non-transitory computer readable medium encoded with instructions for obtaining an image of an object, wherein the image includes Q lines of image data, wherein each line of image data is associated with a position of a scanner, the instructions comprising: instructions for receiving a first set of H lines of image data which is a subset of the image, wherein the first set of H lines includes one or more lines, and H is less than Q; instructions for receiving a second set of R lines of image data which is a subset of the image, wherein the second set of R lines includes one or more lines, and R is less than R; instructions for detecting a relative change in a position of the object by analyzing the first set of H lines and the second set of R lines; instructions for sending information so that a relative position of the scanner is adjusted to compensate for the detected relative change in the position of the object; instructions for repeatedly receiving additional lines of image data, until a total of Q lines of image data including the H lines of image data and the R lines of image data is received; instructions for repeatedly detecting new relative changes in the position of the object by analyzing the additional lines of image data; instructions for repeatedly sending information so that relative positions of the scanner are adjusted to compensate for the repeatedly detected new relative changes in the position of the object; and instructions for constructing an image with the Q lines of image data, wherein relative positions of each of the Q lines of image data are adjusted relative to each other to compensate for motion of the object. In an alternative embodiment, H is equal to R.

In an alternative embodiment, the relative change in the position of the object is detected by analyzing the first set of H lines and the first set of R lines relative to a reference image of the object.

In an alternative embodiment, the relative change in the position of the object is detected by analyzing the first set of H lines relative to the second set of R lines.

BRIEF DESCRIPTION OF THE DRAWINGS

The accompanying drawings, which are incorporated in and constitute a part of the specification, illustrate exemplary embodiments.

DESCRIPTION OF THE EMBODIMENTS

Figure 1:
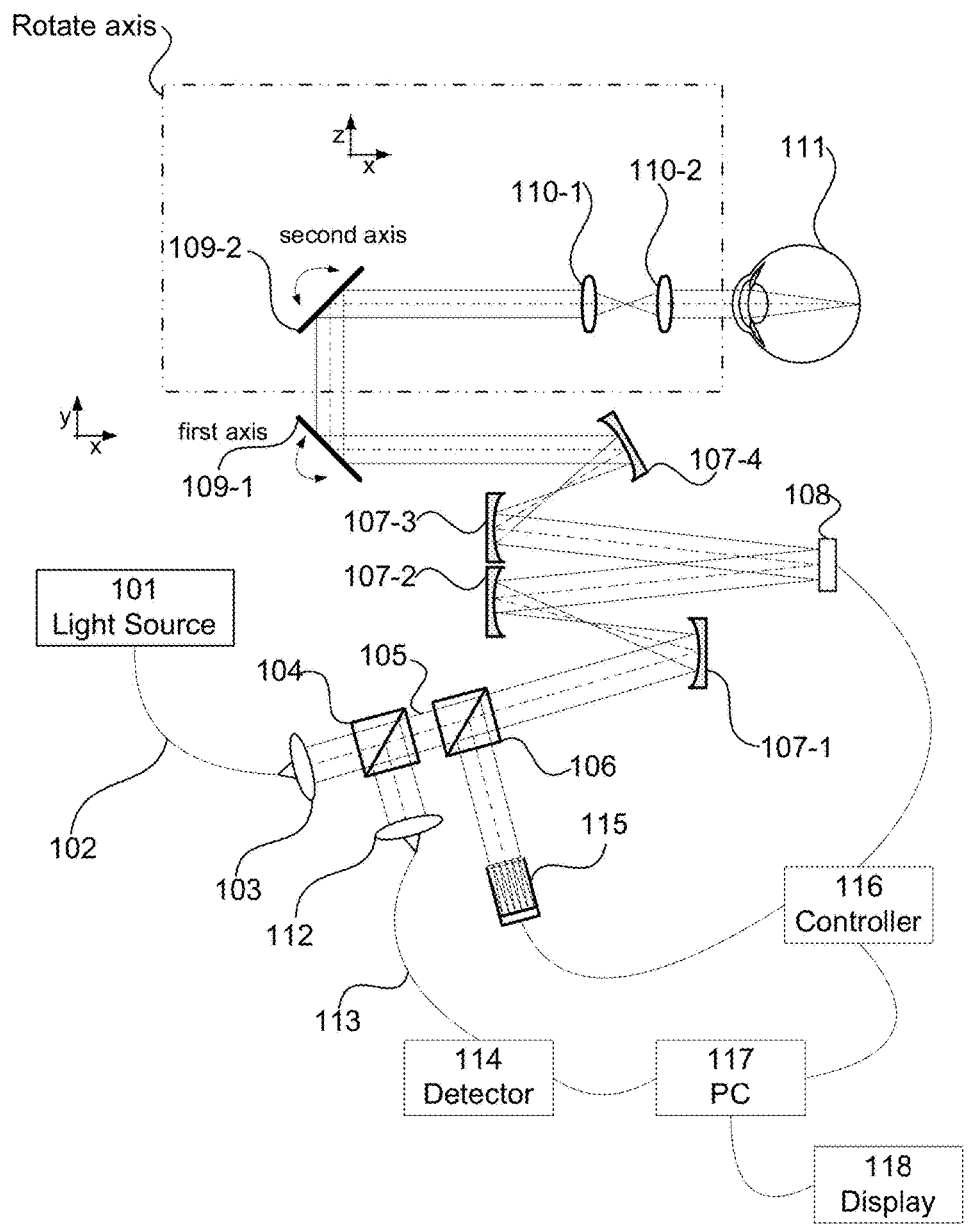
FIG. 1 is an illustration of a first ophthalmoscope in which an embodiment may be implemented.

Embodiments will be described below with reference to the attached drawings. Like numbers refer to like elements throughout. Exemplary embodiments will be described in detail with reference to the drawings below. It shall be noted that the following description is merely illustrative and exemplary in nature, and is in no way intended to limit the disclosure and its applications or uses. The relative arrangement of components and steps, numerical expressions and numerical values set forth in the embodiments do not limit the scope of the disclosure unless it is otherwise specifically stated. Techniques, methods, and devices which are well known by individuals skilled in the art may not have been discussed in detail since an individual skilled in the art would not need to know these details to enable the embodiments discussed below. Further, an image photographing apparatus as disclosed in the following can be applied to an object to be inspected such as an eye to be inspected, skin, and internal organs.

Ophthalmoscope

A first embodiment is described with reference to a fundus image photographing apparatus such as the photographing apparatus illustrated in FIG. 1.

Embodiments are directed towards systems, methods, and software which are used in connection with an imaging system such as an ophthalmoscope. FIG. 1 is an illustration of an exemplary ophthalmoscope. An ophthalmoscope is a system or apparatus for obtaining information about an interior portion of the eye 111 (e.g., the fundus).

An exemplary embodiment may be a scanning ophthalmoscope. A scanning ophthalmoscope scans a spot across the eye. The spot may be a spot of light from a light source that is scanned across the eye.

In an exemplary embodiment, the spot of light is produced by a light source 101. The light source 101 may be incorporated into the ophthalmoscope; alternatively, the ophthalmoscope may include an input for receiving a light source 101. The input for the light source 101 may be a fiber optic input or a free space input. The light source 101 may be a laser, a broadband light source, or multiple light sources. In an exemplary embodiment, the light source 101 is a super luminescent diode (SLD) light source having a wavelength of 840 nm. The wavelength of the light source 101 is not particularly limited, but the wavelength of the light source 101 for fundus image photographing is suitably set in a range of approximately 800 nm to 1,500 nm in order to reduce glare for a person to be inspected and maintain imaging resolution.

In an exemplary embodiment, light emitted from the light source 101 passes through a single-mode optical fiber 102, and is radiated as collimated light (measuring light 105) by a collimator 103.

In an exemplary embodiment, the polarization of the irradiated light may be adjusted by a polarization adjusting member 119 (not shown) provided in a path of the single-mode optical fiber 102. In an alternative configuration, the light source 102 is polarized and single-mode optical fiber 102 is polarization maintain fiber. In another configuration, the polarization adjusting member may be placed after the collimator 103. Alternatively, the polarization adjusting member may be replaced with a polarizer.

The measuring light 105 radiated from the collimator 103 passes through a light division portion 104 including a beam splitter. An exemplary embodiment may include an adaptive optical system. Exemplary embodiments include both systems that do and do not include the adaptive optical system.

The adaptive optical system includes a light division portion 106, a wavefront sensor 115, wavefront correction device 108, and reflective mirrors 107-1 to 107-4 for guiding the measuring light 105 to those components. The reflective mirrors 107-1 to 107-4 are provided to guide the measuring light 105 to and from the pupil of an eye 111, the wavefront sensor 115, and the wavefront correction device 108. The wavefront sensor 115 and the wavefront correction device 108 may be in an optically conjugate relationship. A beam splitter may be used as the light division portion 106. The wavefront sensor 115 may be a Shack-Hartmann sensor.

The measuring light 105 passing through the light division portion 106 is reflected on the reflective mirrors 107-1 and 107-2 to enter the wavefront correction device 108. The measuring light 105 reflected on the wavefront correction device 108 and is further reflected on the reflective mirrors 107-3 and 107-4.

In one embodiment, the wavefront correction device 108 is a deformable mirror. In an alternative embodiment, one or two spatial phase modulators including a liquid crystal element is used as the wavefront correction device 108 which is not illustrated. The liquid crystal element may modulate a phase of only a specific polarized component. In which case, two liquid crystal elements may be employed to modulate substantially orthogonal polarized components of the measuring light 105.

The measuring light 105 reflected off mirror 107-4 is two-dimensionally scanned by a scanning optical system 109 which may be part of a scanning unit. In an exemplary embodiment, the scanning optical system 109 includes a first scanner 109-1 and a second scanner 109-2. The first scanner 109-1 may be part of a first scanning unit. The second scanner 109-2 may be part of a second scanning unit. The first scanner 109-1 rotates around the first axis, while the second scanner 109-2 rotates around a second axis. The first axis is substantially orthogonal to the second axis.

FIG. 1 illustrates the first scanner 109-1 rotating in the x-y plane, while the second scanner 109-2 is rotating in the z-x plane. In the context of the present application, rotating the measuring light 105 in a first plane around the first axis is equivalent to rotating the measuring light 105 in the first plane and is equivalent to scanning the spot of light in the main scanning direction or the lateral direction of the object being imaged. In the context of the present application, rotating the measuring light 105 in a second plane around the second axis is equivalent to rotating the measuring light 105 in the second plane and is equivalent to scanning the spot of light in the sub-scanning direction or the longitudinal direction of the object being imaged. The sub-scanning direction is substantially orthogonal to the main scanning direction.

A scanning period of the first scanner 109-1 is less than the scanning period of the second scanner 109-2. The order of the first scanner 109-1 and the second scanner 109-2 may be exchanged without impacting the operation of an exemplary embodiment. The first scanner 109-1 may operate in a resonant scanning mode.

In an exemplary embodiment, the scanning optical system 109 may be a single scanning mirror that is rotated around the first axis by the first scanner 109-1 and around the second axis by the second scanner 109-2 that is substantially orthogonal to the first axis. An exemplary embodiment may also use non-mechanical beam steering techniques may also be used.

In an exemplary embodiment, the first scanner 109-1 and the second scanner 109-2 are galvano-scanners. In another exemplary embodiment, one of the first scanner 109-1 and the second scanner 109-2 is a resonant scanner. The resonant scanner may be used for the main scanning direction. The resonant scanner may be tuned to oscillate at a specific frequency.

The measuring light 105 scanned by the scanning optical system 109 is radiated to the eye 111 through eyepieces 110-1 and 110-2. The measuring light radiated to the eye 111 is reflected, scattered, or absorbed on the fundus. When the eyepieces 110-1 and 110-2 are adjusted in position, suitable irradiation may be performed in accordance with the diopter of the eye 111. Lenses may be used for the eyepiece portion in this embodiment, but other optical components such as spherical mirrors may also be used.

Reflected light which is produced by reflection or scattering on a retina of the eye 111 then travels in the reverse direction along the same path as in the case of incident light. A part of the reflected light is reflected by the light division portion 106 to the wavefront sensor 115 to be used for measuring a light beam wavefront.

In an exemplary embodiment, a Shack-Hartmann sensor is used as the wavefront sensor 115. However, an exemplary embodiment is not limited to a Shack-Hartmann sensor. Another wavefront measurement unit, for example, a curvature sensor may be employed or a method of obtaining the wavefront by reverse calculation from the formed spot images may also be employed.

In FIG. 1, when the reflected light passes through the light division portion 106, a part thereof is reflected on the light division portion 104 and is guided to a light intensity sensor 114 through a collimator 112 and an optical fiber 113. The light intensity sensor 114 converts the light into an electrical signal. The electrical signal is processed by a control unit 117 into an image of the object, and the image is displayed on a display 118.

The wavefront sensor 115 is connected to an adaptive optics control unit 116. The received wavefront is transferred to the adaptive optics control unit 116. The wavefront correction device 108 is also connected to the adaptive optics control unit 116 and performs modulation as instructed by the adaptive optics control unit 116. The adaptive optics control unit 116 calculates a modulation amount (correction amount) for correction to obtain wavefront having no aberration based on the wavefront obtained by a measuring result of the wavefront sensor 115, and instructs the wavefront correction device 108 to perform the modulation according to the modulation amount. The wavefront measurement and the instruction to the wavefront correction device are repeated and feedback control is performed so as to obtain a suitable wavefront.

In an exemplary embodiment the light division portion 104 is a fused fiber coupler. In an alternative exemplary embodiment, the light division portions 104 and 106 include partially reflective mirrors.

The detector 114 may detect reflections or fluorescence associated with the scanning spot. The detection system may make use confocal microscopy techniques in which an aperture associated with the scanning spot is used to increase the resolution and/or contrast of the detection system. The system may also include a reference arm and the detection system may be used to detect an interference signal.

Figure 2A:
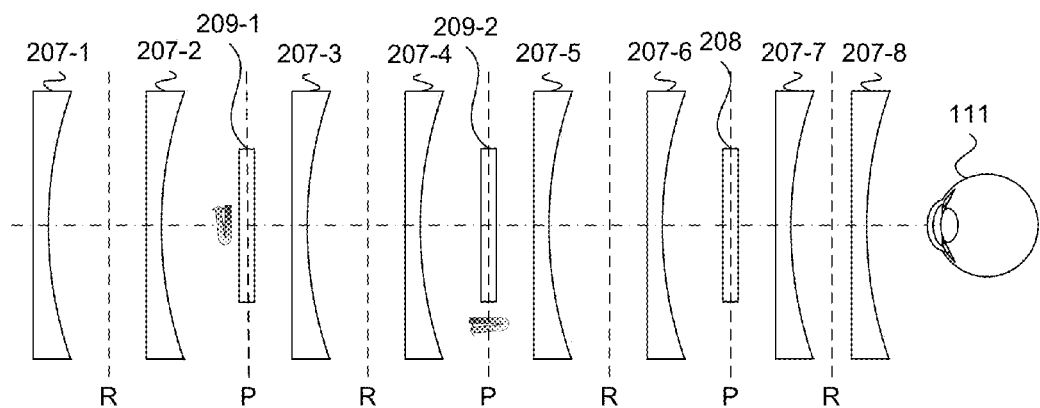
FIG. 2A is an illustration of a schematic optical layout of a first embodiment.

FIG. 2A is a schematic optical layout showing the order of components in an AO-SLO system 200 in which two 1D scanners are used for 2D imaging an interior portion of the eye 111. The AO-SLO system 200 includes 8 reflective mirrors 207-1-207-8. The reflective mirrors 207-1-207-8 may be spherical and/or aspherical mirrors. The reflective mirrors 207-1-207-8 are arranged so as to form pupil conjugate planes (P) and retinal conjugate planes (R) as illustrated in FIG. 2A. The AO-SLO system 200 includes a first scanner 209-1 and a second scanner 209-2. The first scanner 209-1 may be part of a first scanning unit. The second scanner 209-2 may be part of a second scanning unit. The first scanner 209-1 rotates around the first axis, while the second scanner 209-2 rotates around a second axis. The first axis is substantially orthogonal to the second axis. The first scanner 209-1 may be a fast scanner and the second scanner 209-2 may be a slow scanner. The AO-SLO system 200 includes a wavefront correction device 208. The wavefront correction device 208 may be positioned before or after the first scanner 209-1 and the second scanner 209-2. The first scanner 209-1, the second scanner 209-2, and the wavefront corrector 208 may all be located on pupil conjugate planes P.

Figure 2B:
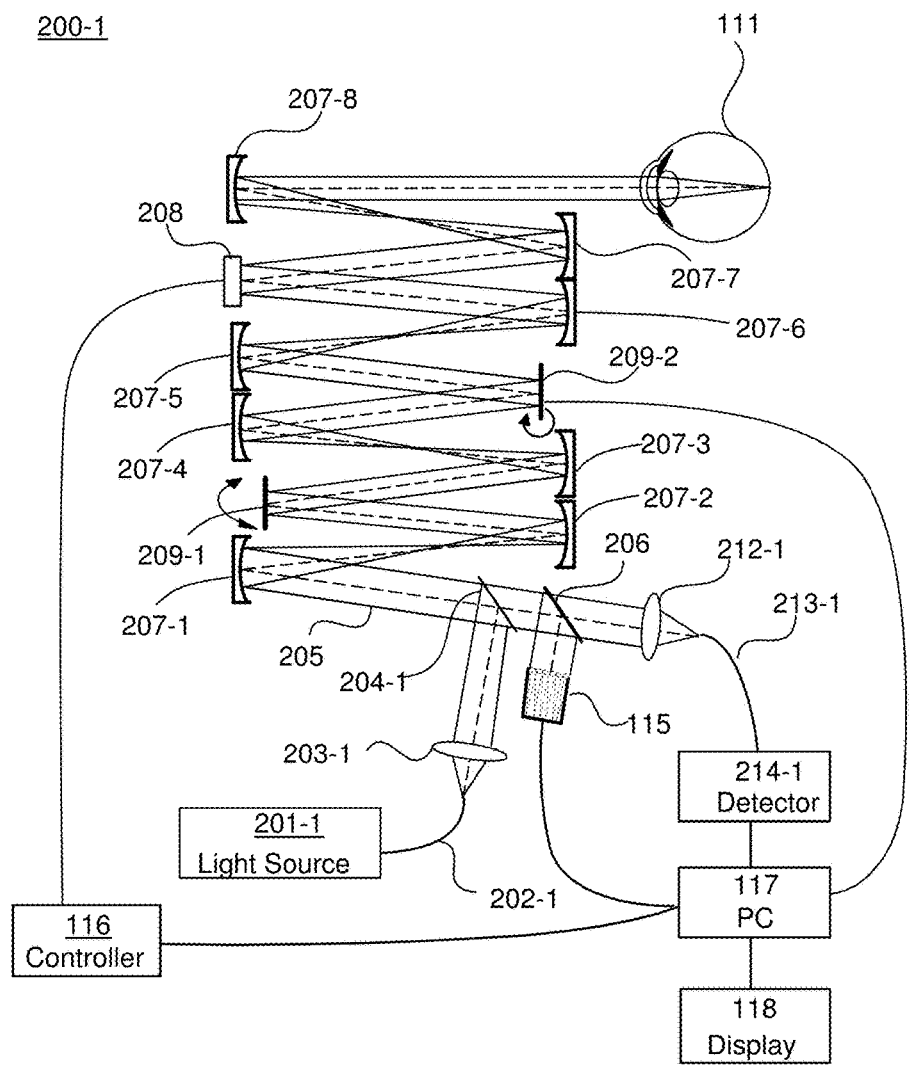
FIG. 2B is an illustration of an ophthalmoscope in which a first embodiment may be implemented.

FIG. 2B is an illustration of an embodiment 200-1 showing optical system 200 in which the arrangement of additional components are illustrated including: a light source 201-1, fibers 202-1 and 213-1, lenses 203-1, 212-1, light division units 204-1 and 206-1, detector 214-, a wavefront sensor 115, a controller 116, PC 117 and a display 118.

The light source 201-1 emits light 205 which may be passed to optical system 200 via optical fiber 202-1. The lens 203-1 may be used to produce collimated light 205. The collimated light propagates through optical system 200 to the eye 111. The optical system 200 has two single axis optical scanners 209-1 and 209-2 located at the positions optically conjugate with the pupil 111 of the eye as described above.

The first scanner 209-1 scans the incident beam with respect to the first scan direction. The first scan direction is perpendicular to rotation axis of the first scanner 209-1. The second scanner 209-2 scans the beam from the first scanner and scans the beam in a second scan direction that is perpendicular to the rotation axis of the second scanner. The second scan direction is perpendicular to the first scan direction. As a result, the beam is incident upon the eye 111 and is focused on the retina while being scanned two dimensionally across the eye.

The light reflected from the retina propagates inversely along the same optical path and is focused by lenses 212-1 onto fiber 213 and is collected by the detector 214-1. The light signal from the eye 111 is thus detected and converted into an electrical signal which is sent to the PC 117.

The electrical signal from the detector 214-1 is synchronized with the scan timing signals from the two scanners 209-1 and 209-2 by the PC 117. This allows the PC 117 to form a two dimensional AO-SLO image which can be used to form a video signal with N scan lines. The PC 117 may cause the display 118 to display the AO-SLO image and/or video. Alternatively, the image and/or video may be stored in a database and/or as file in a memory system.

The PC 117 calculates the amplitude of the eye movement from the captured video and controls the angle of the second scanner 209-2. This configuration implements the AO-SLO with one dimensional retinal tracking using AO-SLO video itself. Before the light reflected from the eye passes though lens 112-1 a portion of the light is split off by light division unit 206 and is sent to the wavefront sensor 115. The wavefront sensor 115 may be a Shack-Hartmann wavefront but other wavefront sensors may be used without going beyond the scope of the present disclosure.

The PC 117 receives the wavefront information from the wavefront sensor 114 and calculates a modulation amount (correction amount) that can compensate for deviations in the wavefront. The PC 117 sends the modulation amount to the controller 116. The controller 116 instructs the wavefront correction device 208 to perform modulation based on the modulation amount (correction amount) calculated by the PC 117.

When imaging live retinas with AO-SLO 200, images move randomly due to eye motion. This random eye motion causes unsuccessful AO-SLO imaging under cases of poor fixation, and requires a large amount of time for post processing of the raw video files to obtain usable information. Instead of doing post-processing, a real-time optical eye tracking technique using a tracking mirror reduces eye motion dynamically. Such that the residual eye motion will be significantly smaller than the original eye motion. Post-processing requirements can thus be reduced or skipped completely.

Eye motion is a major impediment to the efficient acquisition of artifact-free high resolution retinal images with the adaptive optics scanning light ophthalmoscope AO-SLO 200. Because the eye moves in two-dimensional space, the tracking system also needs to have tracking capability in two perpendicular directions, naturally, at the directions of slow scanning and fast scanning. The following embodiments are solutions to this problem that can combine both optical and digital image stabilization in an AO-SLO 200.

First Embodiment

In a first embodiment eye tracking is implemented using the slow scanner 209-2 for 1D optical tracking in the scanning direction of the slow scanner 209-2. This scanner works in a closed loop for optical eye tracking. Digital stabilization is used to compensate for eye movement that is in the scanning direction of the fast scanner 209-1. Digital stabilization may also be used to compensate for eye movement that is in the scanning direction of the slow scanner 209-2. The closed loop optical eye tracking can reduce the magnitude of digital stabilization necessary in the scanning of the slow scanner 209-2 much of the time.

Second Embodiment

Figure 3:
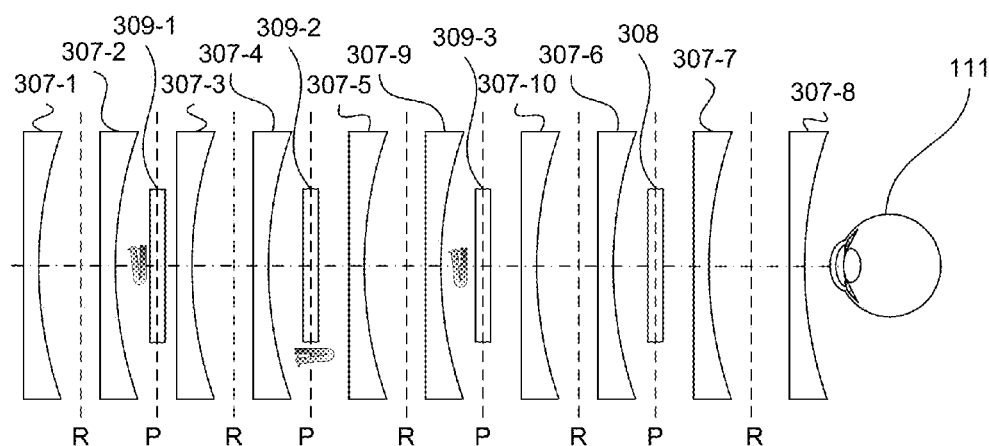
FIG. 3 is an illustration of a schematic optical layout of a second embodiment.

FIG. 3 is a schematic optical layout showing the order of components in a second AO-SLO system 300. The AO-SLO system 300 includes 10 reflective mirrors 307-1-307-10. The reflective mirrors 307-1-307-10 may be spherical and/or aspherical mirrors. The reflective mirrors 307-1-307-10 are arranged so as to form pupil conjugate planes (P) and retinal conjugate planes (R) as illustrated in FIG. 3. The AO-SLO system 300 includes a first scanner 309-1, a second scanner 309-2, and a third scanner 309-3. The first scanner 309-1 may be part of a first scanning unit. The second scanner 309-2 may be part of a second scanning unit. The third scanner 309-3 may be part of a third scanning unit. The first scanner 309-1 rotates around the first axis, the second scanner 309-2 rotates around a second axis, and the third scanner 309-3 rotates around the third axis that is substantially parallel to the first axis. The first axis is substantially orthogonal to the second axis. The first scanner 309-1 may be a fast scanner, the second and third scanners 309-2 and 309-3 may be slow scanners. The AO-SLO system 300 includes a wavefront correction device 308. The wavefront correction device 308 may be positioned before or after the scanners 309-1-3. The first scanner 309-1, the second scanner 309-2, the third scanner 309-3, and the wavefront corrector 308 may all be located on pupil conjugate planes P.

In a second embodiment, the second scanner 309-2, which is a slow scanner, is also used for 1D optical tracking in the scanning direction of the slow scanner 309-2. The third scanner 309-3, which is a slow scanner, is a tracking scanner that is perpendicular to the scanning direction of the second scanner 309-2, or in a direction that is parallel to scanning direction of the first scanner 309-1, which is a faster scanner. The two slow scanners 309-2- and 309-3 work in closed loop operation for optical eye tracking.

Third Embodiment

Figure 4:
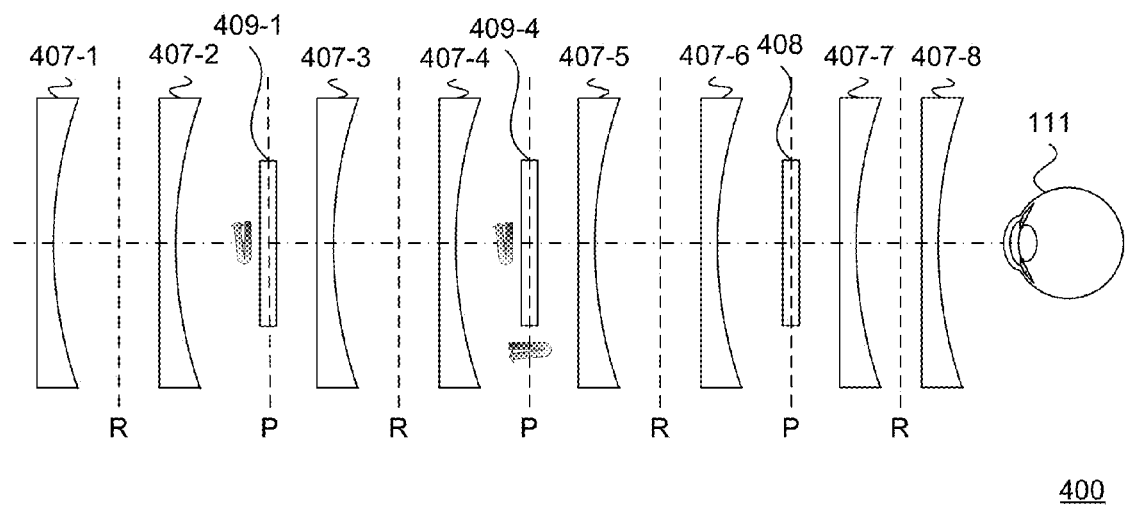
FIG. 4 is an illustration of a third embodiment.

FIG. 4 is a schematic optical layout showing the order of components in an AO-SLO system 400 in which two scanners are used for 2D imaging an interior portion of the eye 111. The AO-SLO system 400 includes 8 reflective mirrors 407-1-407-8. The reflective mirrors 407-1-407-8 may be spherical and/or aspherical mirrors. The reflective mirrors 407-1-407-8 are arranged so as to form pupil conjugate planes (P) and retinal conjugate planes (R) as illustrated in FIG. 4. The AO-SLO system 400 includes a first scanner 409-1 and a second scanner 409-4. The first scanner 409-1 may be part of a first scanning unit. The second scanner 409-4 may be part of a second scanning unit. The first scanner 409-1 rotates around a first axis. The second scanner 409-4 is a 2D tip-tilt mirror that is also used as a slow scanner and rotates which rotates around a second axis that substantially orthogonal to the first axis. The first scanner 409-1 may be a fast scanner. The AO-SLO system 400 includes a wavefront correction device 408. The wavefront correction device 408 may be positioned before or after the first scanner 409-1 and the second scanner 409-4. The first scanner 409-1, the second scanner 409-4, and the wavefront corrector 408 may all be located on pupil conjugate planes P.

In the third embodiment 400, the slow scanner 409-4 is a 2D tip/tilt mirror. This 2D tip/tilt mirror does three jobs: the same slow frame scanning as in the first and second embodiment; tracking in the direction of the slow scanner as in the first and second embodiment; and tracking in the direction of fast scanner 409-1. All parts in the optical system remain the same except the replacement of the existing 1D slow scanner with a 2D tip/tilt mirror. The 2D tip/tilt mirror 409-4 may work in a closed loop for optical eye tracking.

Figure 5:
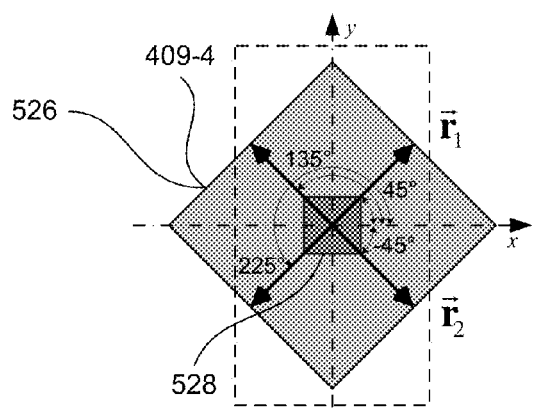
FIG. 5 is an illustration of a tip/tilt mirror.

An example of the second scanner 409-4 is a Physik Instrumente S-334.2SL 2D tip/tilt mirror. Each rotation axis of the 2D tip/tilt mirror has an independent ±3° of optical deflection. When the mirror is mounted at 0° or 90°, the two vectors $\vec{r}_1$ and $\vec{r}_2$ point in the directions of 45° and 135° respectively, as shown in FIG. 5.

For convenience, we define a vector $\vec{r}$ in terms of two unit vectors $\hat{r}_1$ and $\hat{r}_2$ which are defined in equations 1.1-1.3 below.

$$\hat{r}_1 = \frac{\vec{r}_1}{|\vec{r}_1|} \quad (1)$$

$$\hat{r}_2 = \frac{\vec{r}_2}{|\vec{r}_2|} \quad (2)$$

$$\vec{r} = a\hat{r}_1 + b\hat{r}_2 \quad (3)$$

The two vectors $\vec{r}_1$ and $\vec{r}_2$ represent the motions in the individual directions of unit vectors $\hat{r}_1$ and $\hat{r}_2$ for the 2-D tilt mirror 409-4, the vector $\hat{r}$ is the combined motion, and coefficients (a, b) are amplitudes of the vector $\vec{r}$ along the two axes of unit vectors $\hat{r}_1$ and $\hat{r}_2$. In one embodiment, a slow scanner (such as 109-2, 209-2, 309-2, or 409-4) scans the retina in the vertical direction and a resonant scanner (such as 109-1, 209-1, 309-1, or 409-1) scans the retina 111 in the horizontal direction. The 2D tip/tilt mirror 409-4 such as S-334.2SL is made operate like a slow scanner, by applying identical ramp signals on both axes $\hat{r}_1$ and $\hat{r}_2$ of the S-334.2SL, and adjusting both amplitudes by a factor of $\sqrt{2}/2$. The two vectors $\vec{r}_1$ and $\vec{r}_2$ give the tracking range of the 2D tip/tilt mirror 409-4, as illustrated in the diamond area 526 in FIG. 5. The AO-SLO imaging area 528 is illustrated in the dark area in FIG. 5 where the images move randomly due to eye motion. Therefore, as long as images of the eye in the AO-SLO imaging area 528 do not move out of the diamond area 526, the tracking mirror 409-4 will be able to track these motions by updating positions of the AO-SLO imaging area 528 dynamically.

Wide-FOV

Figure 2C:
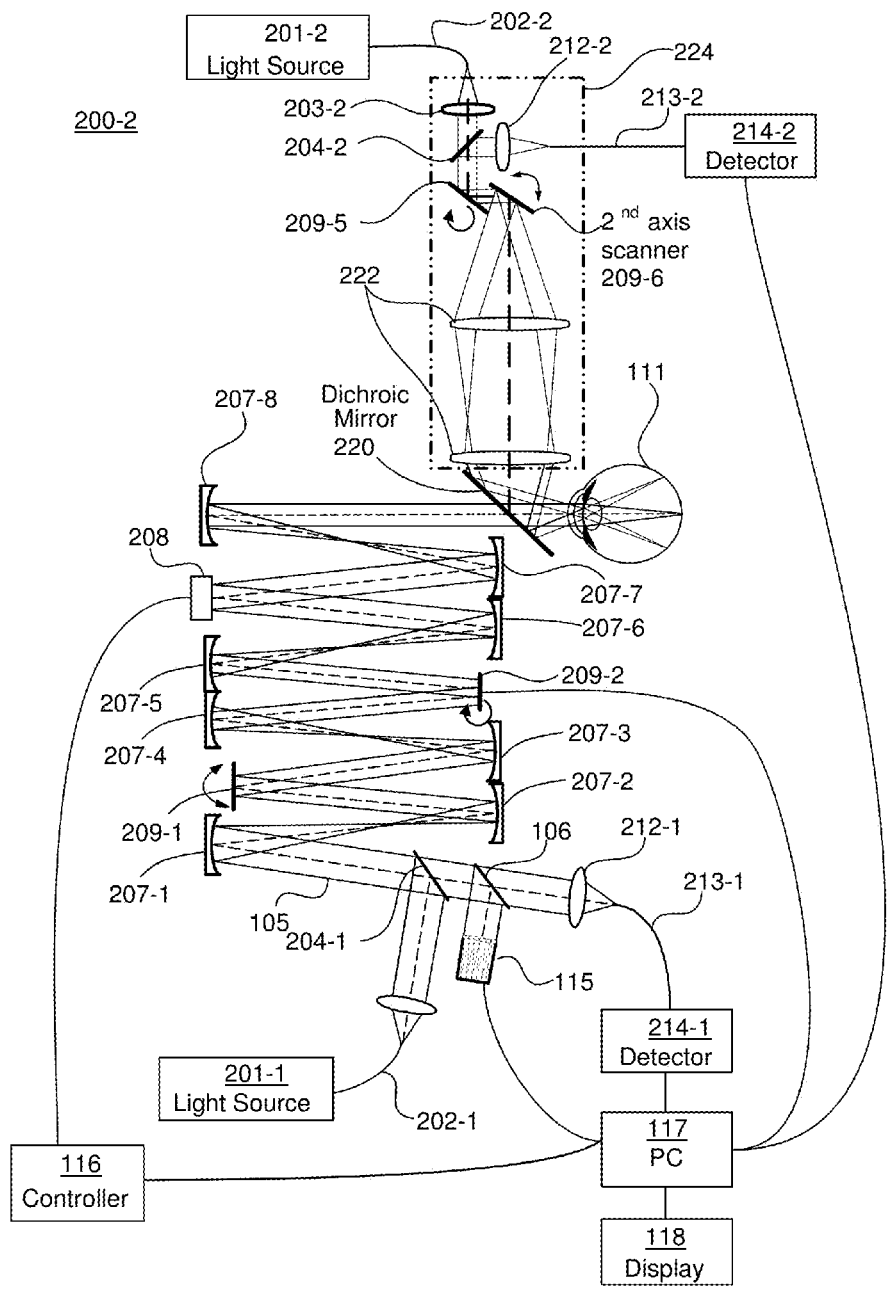
FIG. 2C is an illustration of ophthalmoscope in which a first embodiment may be implemented with a wide field of view.

Especially in case of patients' eye, the area of interest occasionally gets out of the field of view of the AO-SLO optical system due to the large eye movement since AO optical systems typically have small field of view (scanning angle) such as 1°×1°, corresponding to 0.3 mm×0.3 mm image area on the retina. Each of the embodiments may also include a wide-FOV SLO (WF-SLO) subsystem 224 as illustrated in FIG. 2C. An embodiment may include a reflective AO-SLO 200-1 with a FOV of 1.5°×1.5°) and a refractive point-scan WF-SLO 224 with a FOV of 27°×23° which is optically and electronically integrated for rapid, simultaneous data acquisition. A steering mirror may be located at a pupil conjugate plane to allow the AO imaging field to be shifted across 15°. The AO-SLO sub-system 200-1 may have a near diffraction-limited performance across all steering angles.

FIG. 2C is an illustration of an embodiment 200-2 that includes the WF-SLO 224 to follow large eye movements and an AO-SLO subsystem 200-1. The irradiation light for the WF-SLO 224 is from a light source 201-2. The wavelength of the light source 201-2 may be a different wavelength from the wavelength of light source 201-1. The light from the light source 201-2 may pass through optical fiber 202-2 which may then be collimated by lens 203-2. The collimated light then passes through a beam splitter 204-2, which is then scanned on the retina by two scanners 209-5 and 209-6. The scanned light may then passes through lenses 222. After passing through the lenses the light may then pass through or be reflected by a dichroic mirror 220 before being shined onto the eye. In an alternative embodiment, the dichroic mirror may be replaced with a switchable mirror for switching between the WF-SLO 224 and the AO-SLO 200-1. Light from the eye 111 then passes back through the optical system until it reaches the beamsplitter 204-2 which may then pass the light through a lens 212-2 onto a fiber 213-2 and into a detector 214-2. The WF-SLO 224 optics has a large field of view which can cover large eye movements on the retina 111 (such as 6 mm×6 mm). Both AO-SLO 200-1 and WF-SLO 224 optics have a common view axis arranged by the dichroic mirror 220.

The light signal detected by the detector 214-2 is converted into the electric signal and sent to the PC 117. This signal is synchronized with the scan timing signal from the two scanners 209-5 and 209-6 to forms the two dimensional WF-SLO image and/or video. The PC 117 calculates the amplitude of the eye movement from the captured WF video or image and controls the angle of the second scanner 209-2 of the AO-SLO 200-1. This configuration implements AO-SLO with one dimensional retinal tracking using WF-SLO video.

The WF-SLO subsystem may feature 15 μm lateral resolution providing high contrast retinal images in which the optic disk and vasculature are clearly visible. The AO-SLO subsystem may have a focus range of −6.5 diopters (D) to 1.5 D with ~2 μm of lateral resolution. An embodiment may be have a theoretical uncorrected wavefront error at 790 nm of <1.12 waves (peak-to-valley) and <0.24 waves (RMS) across the entire 15° steering field. An embodiment may have the ability to resolve rods and the entire foveal cone mosaic in the eye.

Eye Tracking

The eye tracking control algorithm may be based upon a cross-correlation technique which may be running on a GPU such as an nVidia GPU. A reference frame from the imaging system may be chosen, and subsequent target frames may be registered against this reference frame. The reference frame may be obtained from the WF-SLO or the AO-SLO. An alternative embodiment may include criteria for choosing the reference frame automatically. Increasing the sampling rate of the tracking system decreases the system latency, when calculating eye motion. A single frame with Q scan lines may be divided into multiple strips each with H and/or R lines in which H and R are less than Q. Whenever an image grabber receives a strip of image data, this strip of image data may be sent to a tracking algorithm. The algorithm may be optimized such that in less than 2 milliseconds, eye motion as measured in this strip can be sent to a tracking mirror which starts "pulling back" the eye. Pulling back the eye means moving the tracking mirror such that the motion of the eye as measured in the strip is compensated for by moving the tracking mirror in the opposite direction of the detected movement. The net effect is that the effect of the eye motion can be reduced by ½~¼ by using the control signal from the AO-SLO only. The performance is dependent upon the response time of the tracking mirror. The frequency of the eye motion can thus be corrected by up to N/2 Hz where N is the frame rate of the imaging system or the frequency of the slow scanner. The strip number/size can be optimized to achieve the best optical tracking.

Figure 6:
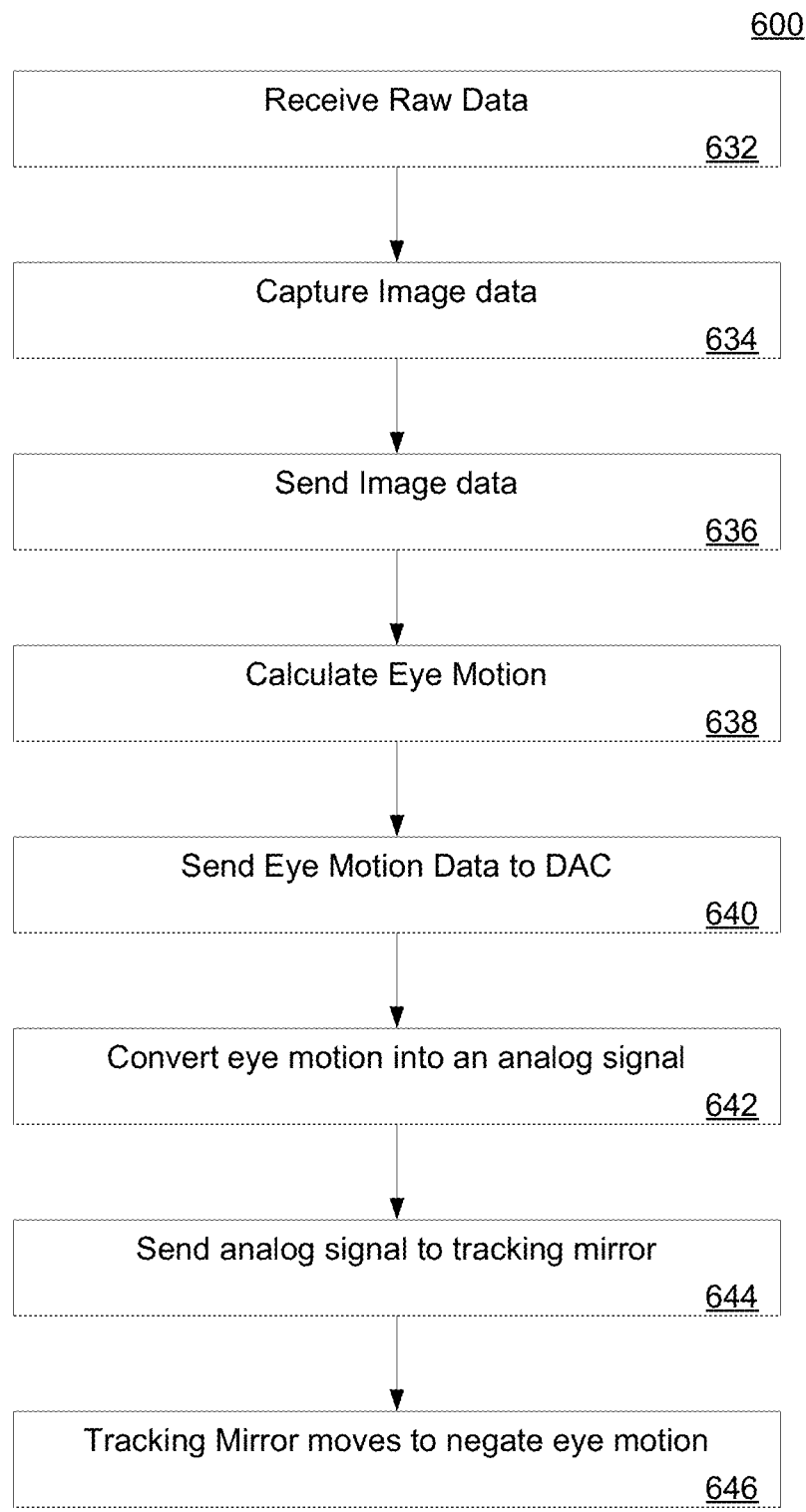
FIG. 6 is a flow chart of an eye tracking method.
Figure 7:
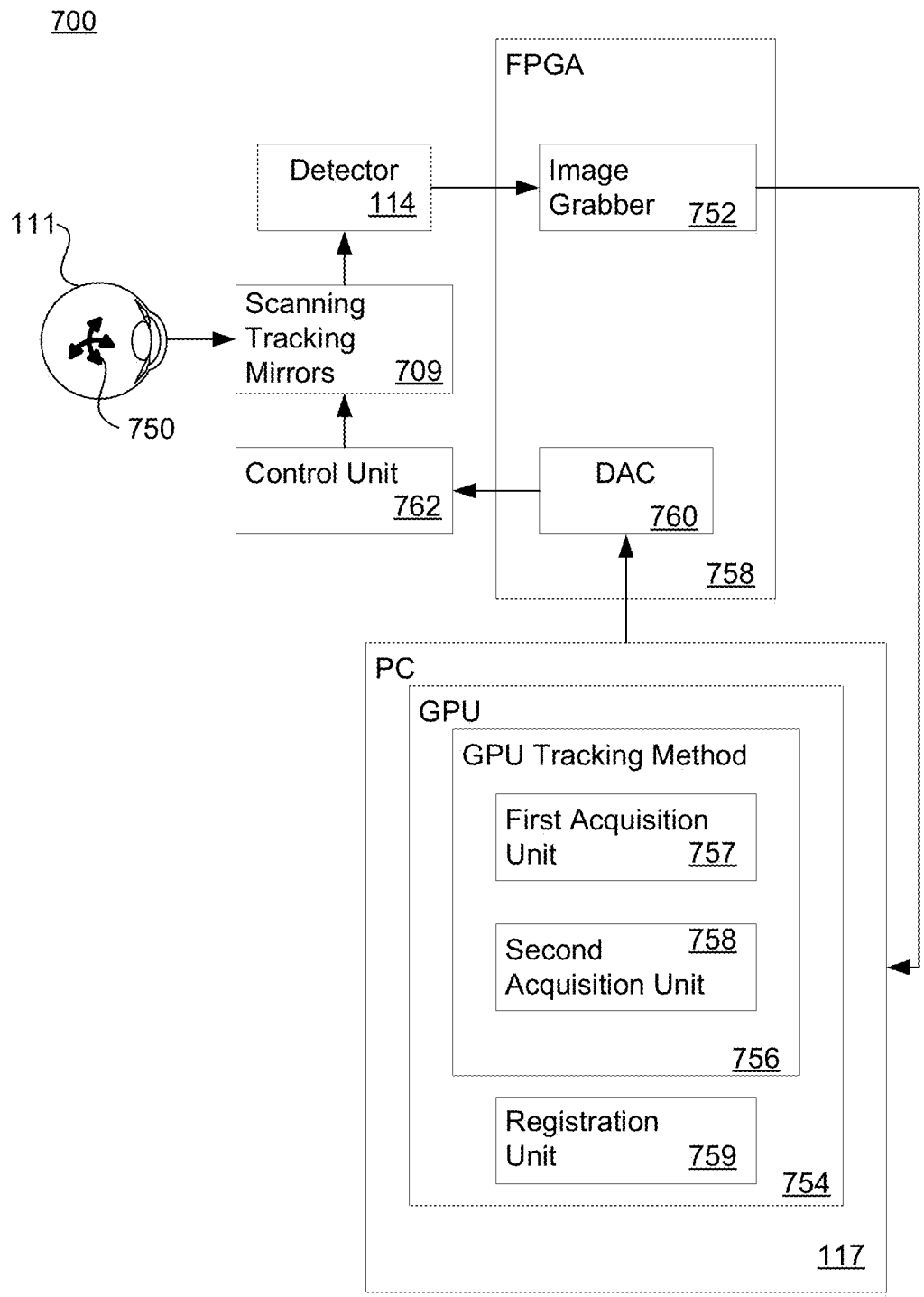
FIG. 7 is an illustration of an system including an embodiment.

FIG. 6 is a flow chart 600 of an eye tracking method as described on a system 700 in FIG. 7. Images of an eye 111 with eye motion 750 are obtained by an optical system which includes scanning unit 709 which includes a plurality of scanners such as tracking and scanning mirrors and are received by the detector 114 such as PMT or APD in a step 632 as raw data. The images of the eye 111 are from light that has been reflected, scattered, or florescence. The detector 114 converts this light into a measurable value such as an analog voltage which is used as raw data.

The scanning unit 709 is an optical system that includes one or more optical components, which may include one or more scanners. The scanning unit 709 receives imaging light and outputs a raster scanned imaging light that is scanned over a scanning area of an object to be imaged. The scanning unit then receives light from the imaging area. The light received from the imaging area, is reflected, scattered, or fluorescent light in response to the raster scanned imaging light. The scanner receives the light from the imaging area and sends it back along the optical path of the received imaging light. The optical components of the scanning unit 709 may include reflective components, refractive components, and/or interference based components. The scanning unit 709 includes a plurality of scanners. The plurality of scanners may include at least a first scanning unit and a second scanning unit. The first scanning unit may be a resonant scanner. The second scanning unit may be a galvano scanner. One or more of the plurality of scanners may be a tip/tilt scanner. One or more of the plurality of scanners may be a linear scanner. One or more of the plurality of scanners may be a MEMS based scanner. One or more of the plurality of scanners may be driven by an electromagnetic force. One or more of the scanners may be an acousto-optic scanner. One or more of scanners may be driven by a capacitive force. One or more of the scanners may be driven by a piezoelectric force. One or more of the plurality of scanners may include a reflective surface. The scanning unit 709 may include one resonate scanner and one galvano scanner.

The raw data is captured as image data by an image grabber 752 in a step 634. The image grabber 752 may include analog to digital converter (ADC). The image grabber 752 may then send the image data to a host PC 117 in a step 636.

Figure 12:
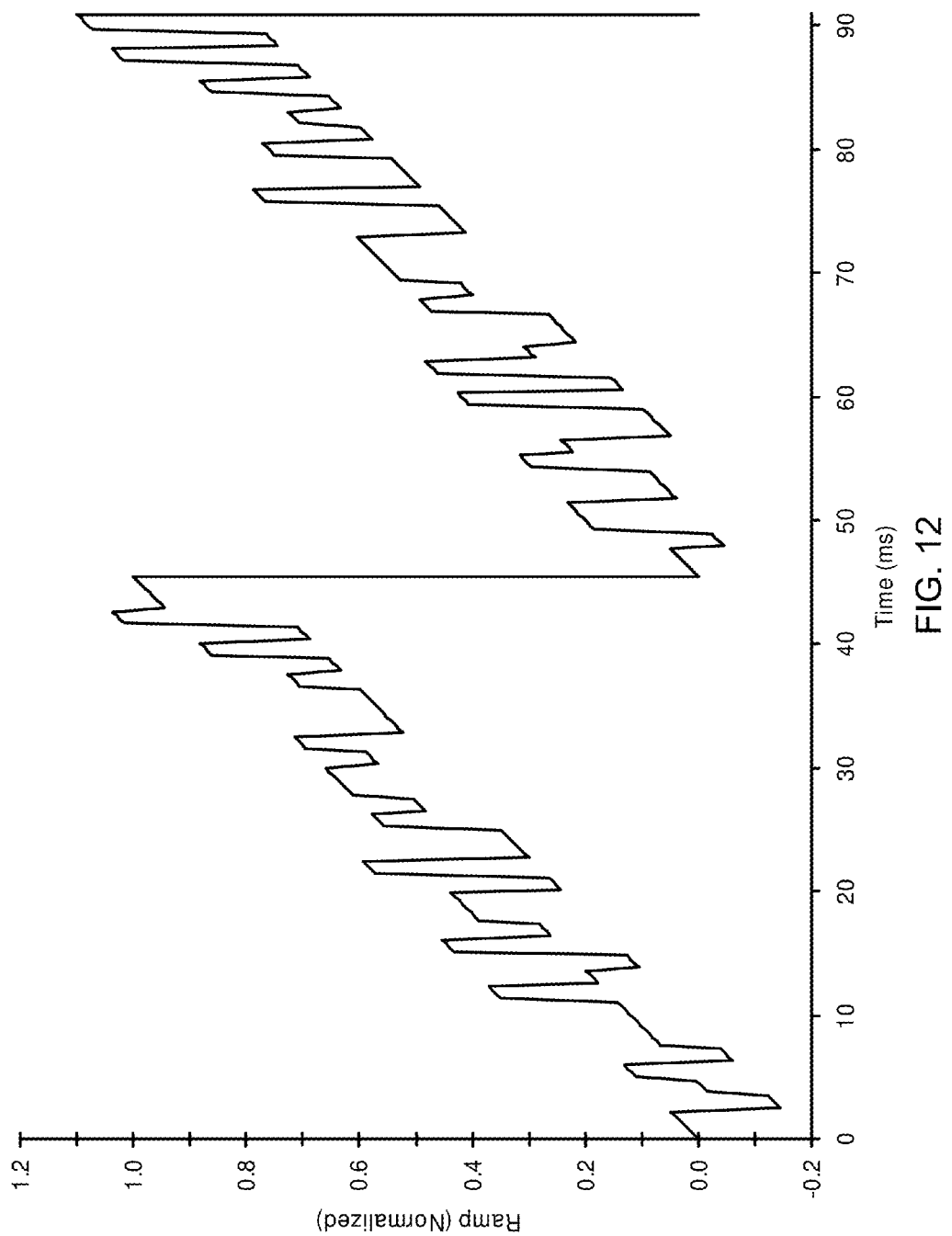
FIG. 12 is an illustration of a ramp signal.

The host PC 117 may calculate a representation of the eye motion 750 as coordinate changes $(x_t, y_t)$ based on the image data calculated in step 638. A GPU 754 on the host PC 117 may be used to calculate the coordinate changes $(x_t, y_t)$ using a GPU based tracking method 756. The tracking method 756 may use a fast Fourier Transform (FFT) based method. The host PC may send the coordinate changes $(x_t, y_t)$ to a Digital-to-Analog converter (DAC) 760 in a step 640. The DAC 760 may be incorporated into the host PC 117 or may be part of a FPGA 758 that includes the image grabber 752. The DAC 760 converts the coordinate changes $(x_t, y_t)$ into an analog voltage in a step 642. The analog signal may then be sent to the electronics of the tracking mirror among the scanning unit 709 that includes a control unit 762, that may include a signal amplifier in a step 644. The tracking mirror moves in response to coordinate changes $(x_t, y_t)$ to negate the eye motion in a step 646. The control unit 762 may include hardware, software, and/or microcode for generating a ramp signal in which a relative offset to the ramp is varied to compensate for a portion of the eye motion 750 as illustrated in FIG. 12. The ramp signal may be a saw tooth wave, a triangle wave, or some other type of ramp signal for moving the mirror.

The FPGA 758 may be a Xilinx ML506 and may be implement the image grabber 752. The DAC 760 may be and the 125MSPS 14-bit DAC such as the Texas Instruments DAC2904EVM. The GPU 754 may be on a consumer level GPU such as the NVIDIA GTX560.

Because of physical latency between motion of the eye and action of the tracking mirror, optical tracking alone does not "freeze" the eye motion, or achieve zero residual eye motion. Digital stabilization may be implemented with a registration unit 759 to register the images. A cross correlation method implemented on the GPU 754 may be used for image registration which may be done in real time. The digital stabilization may be run strip by strip concurrently with the optical tracking, or it may be run at the end of a frame, dependent upon timing from the host PC 117 and the GPU 754. The digital stabilization may be executed with sub-pixel accuracy. The strip size for digital stabilization may be optimized for best image quality, speed, or resource management. The digital stabilization may include adjusting the relative positions of each of the lines of image data relative to each other to compensate for the eye motion 750 of the eye 111.

In a video rate imaging system, an image grabber 752 may send the data to the PC 117 frame by frame. The motion from a 30 fps video may appear smooth, but distortion can be quite obvious in an AO-SLO 200 system due to the scanning mechanism and small field of view. Distortions can be introduced into each frame because the eye 111 moves faster than the frame rate and these distortions are amplified as the FOV becomes smaller.

To increase the sampling rate and reduce electronic latency, images may be transferred from the image grabber 752 to the host PC 117 strip by strip instead of frame by frame. For example, the frame size may be 576×576 pixels at 22 frames per second (fps). Each frame may be divided into 36 strips of 16 lines each, with a strip size of 576×16 pixels. When the resonant scanner is running at 14-16 kHz, the data acquisition time of a 16-line strip is about 1 millisecond, which allows the tracking mirror is updated at a rate of 1 kHz.

When an image-based tracking method such as cross-correlation method is used, these 'within-frame' distortions, effectively encode the motion 750 of the eye 111 during the frame. The motion 750 can be recovered by dividing a whole frame into multiple strips where the motion of each individual strip is calculated separately. A single line of video can be acquired extremely rapidly relative to the eye motion 750 and can be considered to be effectively undistorted (aside from the sinusoidal distortion induced by using a resonate scanner the fast scanner 209-1). Individual strips containing several lines can contain much less distortion than the full frame as they are acquired in a shorter period of time. An entire image can be conveniently registered by calculating and applying the motions from these individual strips. The motion calculated from each strip is sent to the stabilization mirror to steer the imaging beam back to the location of that strip on the reference frame. With zero latency and a perfect motion tracking system, images from the eye will not shift and will be 'frozen' completely when stabilization is engaged. In reality, some residual eye motion will still be seen after optical stabilization is activated due to tracking algorithm errors and the mechanical and electronic latencies. The sources of each of the electronic latencies are listed in Table 1.

TABLE 1

Electronic latencies of the optical stabilization system

| | Duration (ms) | (Source | Description |
|---|---|---|---|
| $T_1$ | ~1.1 | Data acquisition | Sampling time for one strip of data |
| $T_2$ | ~0.07 | Data buffering | Transit time from A/D to GPU |
| $T_3$ | ~0.25 | Preprocessing | Desinusoiding & denoising |
| $T_4$ | ~0.25 | Large amplitude motion & blink detection | Runs concurrently with $T_5$ |
| $T_5$ | ~0.25 | Small amplitude motion | Runs concurrently with $T_4$ |
| $T_6$ | ~0.06 | Eye motion encoding | Converts digital motion (x, y) to voltage (X, Y) to drive stabilization mirror |

To achieve robust cross-correlation, a Gaussian filter may be applied in preprocessing step $T_3$ this makes the cross-correlation algorithm more robust to random noise. In some extreme cases, a Sobel filter may be applied after the Gaussian filter to retrieve features from low-contrast images. Fast, parallel, convolution may be implemented for the Sobel and Gaussian filtering. $T_4$ and $T_5$ are the latencies associated with the main components of the tracking algorithm.

Figure 9:
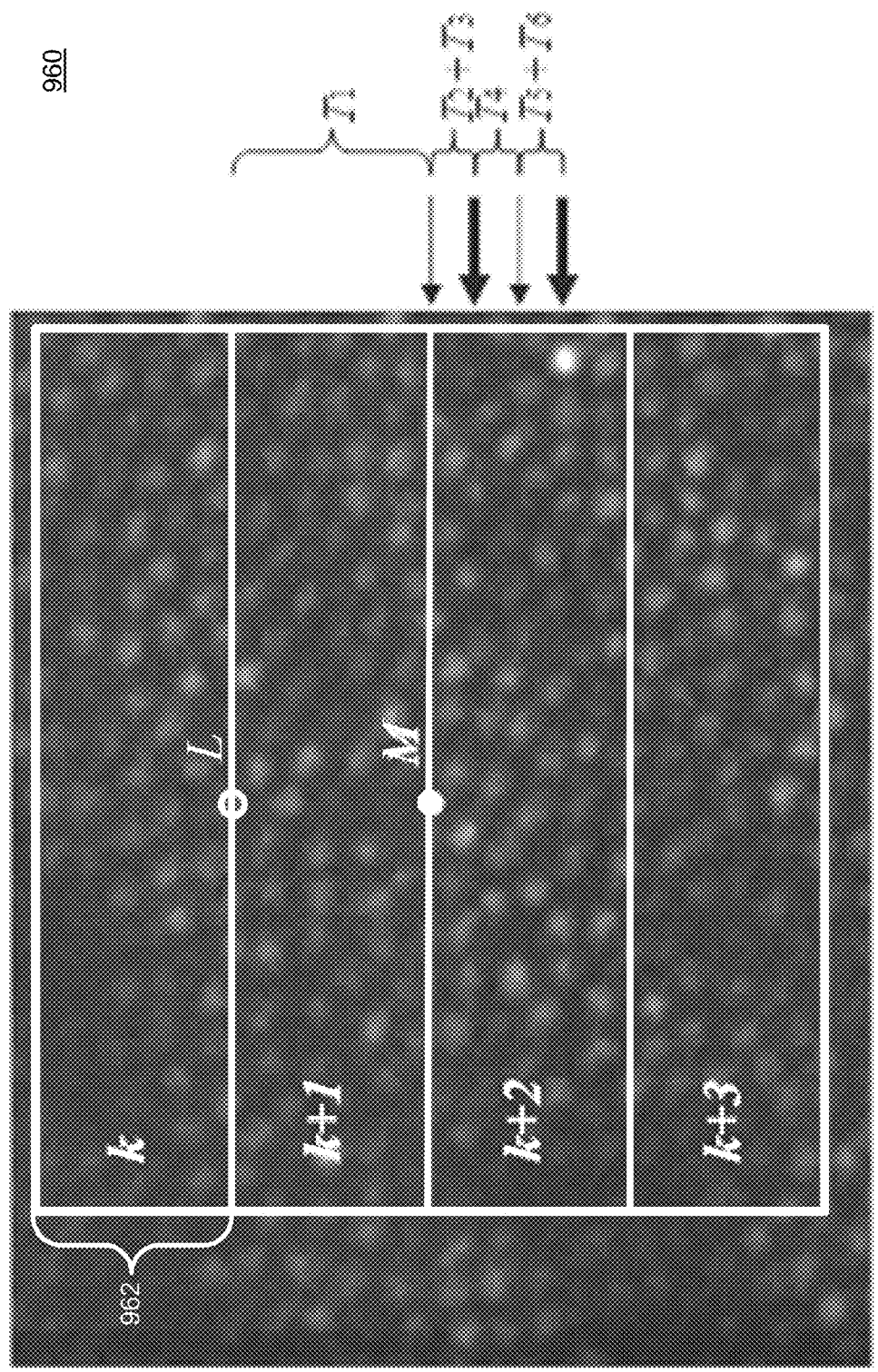
FIG. 9 is an illustration of a frame.

To reduce the data acquisition latency $T_1$, strip-level data acquisition can be implemented as illustrated in a frame 960 shown in FIG. 9. Each frame 960 may be divided into multiple strips 962 and the FPGA 758 can send a single strip 962 to the PC 117 as soon as the analog signal is digitized. The PC 117 then activates the tracking method 756 after the new strip 962 is received. The tracking method 756 includes a first acquisition unit 757 that obtains each strip 962. The first acquisition unit 757 may be implemented in hardware, software, or a combination of software and hardware. The tracking method 756 may also include a second acquisition unit 758 which acquires additional information in which the motion information 750 is encoded. The second acquisition unit 757 may be implemented in hardware, software, or a combination of software and hardware. For example, the second acquisition unit 757 may obtain a neighboring or overlapping strip in which movement can be estimated by comparing the strips using one or more various methods to calculate the coordinate changes ($x_t$,$y_t$). This may be done by measuring the changes relative to a reference frame. If the images were sent to the PC 117 frame by frame, $T_1$ would be at least half the frame rate (i.e. ~16.5 ms for a 30 fps system). After adding $T_2$, $T_3$, $T_4$, $T_5$, and $T_6$ for all the strips of a single frame, the total electronic latency would be >30 ms, which would be too long to realize real-time stabilization. In an alternative embodiment, buffering may be done line-by-line, such that FPGA 758 will send a single line of video data to the PC. In another alternative embodiment, buffering may be done pixel-by-pixel, such that FPGA may send individual pixels to PC 117. The GPU tracking method 754 may be implemented on the GPU 754, a general purpose CPU on the PC 117, a purpose built custom processor, a DSP, or a FPGA.

Strip-level data acquisition and buffering are balanced by two factors: 1) the capability of the PC 117 to handle hardware interrupts; and 2) the minimum amount of data required for robust cross-correlation eye tracking method. When the image grabber 752 sends a strip 962 to the PC 117, it invokes a hardware interrupt so the PC 117 interrupt handler copies the image data from the image grabber 752 to the PC 117. Our benchmarking shows that at the rate of 1000 interrupts/second, the PC 117 uses only ~3-5% of its CPU resources (e.g. on Intel i3, i5, and i7 CPUs); at the rate of 10,000 interrupts/second, the PC 117 uses ~50-70% of its CPU resources, which causes serious reliability issues in smoothly scheduling the other PC 117 threads such as preprocessing and eye motion detection. In one embodiment, the data acquisition strip height is set to 16 lines, this corresponds to ~900 interrupts/second for 576×576 pixel images acquired at 22 Hz.

FIG. 9 is an illustration of the strip-level data acquisition, buffering, and eye motion detection with the six electronic latencies. The duration of the longest latencies ($T_1$, $T_3$, $T_4$, and $T_5$) are denoted by the brackets; arrows denote the end of each latency relative the scanning position. Note that $T_2$ and $T_6$ are extremely short; their durations are denoted by the thickness of the labeled arrows in FIG. 9. Each frame 960 is divided into multiple strips 962, with strip indices k, k+1, k+2, k+3, . . . k+n with H lines per strip. To calculate eye motion at location L (the hollow circle in FIG. 9), cross-correlation requires 2H lines to achieve a robust result, using one strip from the existing data (k) and one strip from the just acquired data (k+1). Therefore, the algorithm obtains sufficient data for cross-correlation after strip k+1 is completely received. In our case, the time to collect strip k+1 with H=16 lines is ~1.1 ms, therefore $T_1$=1.1 ms. After strip k+1 is acquired, data is buffered ($T_2$), and the algorithm proceeds with preprocessing ($T_3$), large amplitude motion & blink detection ($T_4$), small amplitude eye motion calculation ($T_5$) and mirror motion encoding ($T_6$). The computations for $T_3$, $T_4$, and $T_5$ are offloaded to the GPU; each step takes ~0.2-0.25 ms. To save time, the computations for $T_4$ and $T_5$ run in parallel. All of these computations can conveniently be migrated to a CPU if and when future processors become powerful enough. Taking into account an event-driven operating system such as Microsoft Windows 7, the total computational and buffering latency is $T_c=T_2+T_3+T_4+T_5+T_6$ is ~0.7-0.8 ms. From FIG. 9, it can be seen that to run in real-time, $T_c$ must be less than $T_1$, as all computation must be completed before the algorithm receives the next strip of data, strip k+2, which is required to calculate the eye motion one strip below location L (solid circle M in FIG. 9). The total electronic latency ($T_1+T_2+T_3+T_4+T_5+T_6$) is ~1.8-1.9 ms. Thus, the stabilization mirror 409-4 will receive commands ~1.8-1.9 ms after the eye moves. The mechanical latency of the stabilization mirror is ~2 ms. Therefore, the stabilization mirror 409-4 can steer the beam back to its original (reference) location ~4 ms after the eye moves.

The imaging-based tracking system may suffer "frame-out" issues with signal tracking from the AOSLO only. Due to poor fixation, images from the subjects may keep drifting due to eye motion 750 and it is typical that the drifting amount is larger than one frame size. To solve this problem, a wide FOV system, which scans the eye across 20°~30° degrees, is integrated into the AOSLO to track eye motion in real time with the same tracking algorithm. Control signals from the wide FOV system can be applied on the same tracking mirror(s) to reduce eye motion and to avoid frame out. Wherein "frame out" is when the portion of the eye being imaged moves out of frame. Therefore, the tracking mirror(s) receive two sets of control signals, one from AOSLO in a closed loop control method, and the other from the wide FOV system in a closed loop or open loop control method. An apparatus can thus be optimized to produce a cost effective, efficient, and accurate tracking system for SLO. None or only small hardware changes are needed for to add the tracking capability. It can be achieved by using the slow scanner of SLO as a tracking mirror.

SLO slow scanner can be used as a tracking mirror for one direction of eye movement. The other direction of eye movement can be compensated for by image based tracking. This kind of tracking system does not need any hardware modification.

If a 2D tip/tilt mirror is used instead of the galvano scanner for slow scanning, this 2D tip/tilt mirror can take care of slow scanning and tracking in both directions of eye movement. This kind of tracking system doesn't require any modification to the general optical system setup.

If additional galvano scanner is used, the slow scanner can take care of one direction of eye movement and the additional scanner can take care of the other direction of eye movement. This kind of tracking system needs only a small optical modification compared to a 2 galvano scanner tracking system.

As described above the usual pupil conjugate slow scanner (109-2 or 209-2) may be replaced with a 2D tip/tilt mirror 409-4 which may be fast that can have the dual functions of slow scanning and optical eye tracking. Closed-loop optical tracking using these embodiments can be capable of reducing the amplitude of fixational eye motion by a factor of 2.0-4.0 or 10-15 dependent on the step response of the 2D tip/tilt mirror. The residual error is about 3-5 μm with typical fixational eye motion and slightly more with poor fixation. The optical tracking can be capable of correcting the frequency of eye motion up to N/2 Hz where N is the frame rate of the imaging system. Digital stabilization, which may be used in addition to closed loop mechanical tracking, can in real-time can pick up and correct the residual eye motion with a sub-pixel accuracy of 0.4~0.8 μm.

The control algorithm may have difficulty resetting the position of the tracking mirror after a saccade or a blink and can suffer the disadvantages of frame-out. This may be due to the fact that the algorithm cannot correct for movements that are larger than the small) (1.5°×1.5°) AO-SLO field of view. A wide field-of-view (wide-FOV) system, with a 20-30° scanning angle can solve this problem. The wide-FOV system joins the eye tracking system so that the integrated system is capable of significantly improving efficiency of AO-SLO imaging in both normal and diseased eyes even with poor fixation due to retinal diseases.

One or more components of the eye tracking method illustrated in flowchart 600 in FIG. 6 may be implemented as instructions encoded onto a non-transitory computer readable medium. The non-transitory computer readable medium may be for example, a magnetic disk (e.g., a floppy disk, a hard disk), an optical disc (e.g., a CD, a DVD, a Blu-ray), a magneto-optical disk, a magnetic tape, semiconductor memory (e.g., a non-volatile memory card, flash memory, a solid state drive, SRAM, DRAM), an EPROM, an EEPROM, etc. The non-transitory computer readable is configured to store information and/or instructions which can be read and used by one or more processors.

The non-transitory computer readable medium may be encoded with instructions for obtaining an image (such as image 960) of an object (such as an eye 111). The image 960 includes Q lines of image data. Each line of image data is associated with a position of the second scanner 209-2. The instructions for obtaining an image includes instructions for receiving a first set of H lines of image data 960 which is a subset (k) of the image 960, wherein the first set of H lines includes one or more lines, and H is less than Q. The instructions for obtaining an image includes instructions for receiving a second set of R lines of image data which is a subset (k+1) of the image 960, wherein the second set of R lines includes one or more lines, and R is less than Q. The instructions for obtaining an image include instructions for detecting a relative change in a position of the object by analyzing the first set of H lines and the second set of R lines. The instructions for obtaining an image include instructions for sending information so that a relative position of the scanner is adjusted to compensate for the detected relative change in the position of the object. The instructions for obtaining an image includes instructions for repeatedly receiving additional lines of image data, until a total of Q lines of image data including the R lines of image data and the H lines of image data is received. The instructions for obtaining an image include instructions for repeatedly detecting new relative changes in the position of the object by analyzing the additional lines of image data. The instructions for obtaining an image include instructions for repeatedly sending information so that relative positions of the scanner are adjusted to compensate for the repeatedly detected new relative changes in the position of the object. The instructions for obtaining an image includes instructions for constructing an image with the Q lines of image data, wherein relative positions of each of the Q lines of image data are adjusted relative to each other to compensate for motion of the object.

In an alternative embodiment R is equal to H. Alternatively, R is not equal to H, such that the strips 962 sent to the PC 117 are not of equal size.

In an alternative embodiment the relative change in the position of the object is detected by analyzing the first set of H lines and the second set of R lines relative to a reference image of the object.

In an alternative embodiment the relative change in the position of the object is detected by analyzing the first set of H lines relative to the second set of R lines.

Closed-Loop Optical Stabilization

Closed loop optical stabilization may be implemented using closed-loop control as described by equations (4) and (5).

$$T_x(t+1) = T_x(t) + g_x \cdot \Delta x(t) \tag{4}$$

$$T_y(t+1) = T_y(t) + g_y \cdot \Delta y(t) \tag{5}$$

Where the subscripts x and y may denote eye motion in the horizontal (fast scanning) and the vertical (slow scanning) directions, t and t+1 denote time sequence, $g_x$ and $g_y$ are control gains in the two directions, $\Delta x(t)$ and $\Delta y(t)$ are residual eye motions in the two directions calculated from the tracking algorithm, $T_x(t)$ and $T_y(t)$ are the current position of the stabilization mirror, and $T_x(t+1)$ and $T_y(t+1)$ are the new positions of the stabilization mirror. As mentioned previously, the two axes of the stabilization mirror 409-4 may point to 45° and 135°, as shown in FIG. 5, thus $T_x(t+1)$ and $T_y(t+1)$ need to be rotated 45° before they are applied. The stabilization mirror 409-4 is also used simultaneously for slow scanning, so the net signals applied on the two axes of the stabilization mirror are described by equations (6) and (7).

$$S_{400\_r1} = S_x + \Theta\{T_x(t+1)\} \tag{6}$$

$$S_{400\_r2} = S_y + \Theta\{T_y(t+1)\} \tag{7}$$

Where $\Theta$ is the operator of 45° rotation, and $S_x$ and $S_y$ are the slow scanning ramp signals. $S_{400\_r1}$ is the total ramp signal provided along the $\hat{r}_1$ axis of scanner 409-4 of embodiment 400. $S_{400\_r2}$ is the total ramp signal provided along the $\hat{r}_2$ axis of scanner 409-4 of embodiment 400. Due to the relatively slow mechanical response of the stabilization mirror (~2 ms) and the fast eye motion update rate from the tracking algorithm (~1.1 ms), the gain, $g_x$ and $g_y$ may be set to ~0.1-0.15 to achieve stability.

In the alternative embodiment 200 equation 6a is used to in closed loop feedback with scanner 209-2. In the alternative embodiment 300, equation 6a is used to in closed loop feedback with scanner 309-2 and equation 7a is used in closed loop feedback with the third scanner 309-3. In which $S_{200x}$ is the total ramp signal provided along the scanning axis of scanner 209-2 of embodiment 200. FIG. 12 is an illustration of a ramp signal $S_{200x}$. In which $S_{300x}$ is the total ramp signal provided along the scanning axis of scanner 309-2 of embodiment 300. In which $S_{300y}$ is the total ramp signal provided along the scanning axis of scanner 309-3 of embodiment 300.

$$S_{200x} = S_{300x} = S_x + T_x(t+1) \tag{6a}$$

$$S_{300y} = T_y(t+1) \tag{7a}$$

Digital Image Registration

Once the optical stabilization method is being used and the mirror 409-4 dynamically compensates for the eye motion. As described in Equations (4) and (5), the tracking algorithm calculates residual eye motion only. Residual motion is significantly smaller than the raw motion before optical stabilization. Digital image registration uses this small residual motion signal to create an image sequence that is in register. The computational accuracy of the digital registration may be 1 pixel. Digital registration may be executed during the period when the fast scanner 409-2 is moving backward (i.e. after a full image has been acquired but before the next image is acquired). No additional cross correlation is required for digital registration because the motion of any strip from the current frame is calculated before it is used to drive the stabilization mirror. The motions from all the strips are used directly for digital registration at the end of this frame.

Tracking Performance

To demonstrate performance of optical tracking, we start with a model eye whose motion is modulated by a sinusoidal signal from a galvo scanner. The model eye consisted of an achromatic lens and a piece of paper. The performance of optical tracking with 1 Hz and 2 Hz model eye motion, with amplitudes of 0.21° and 0.17°. The results show that residual motion after optical tracking is about 1/12 of the original motion, thus 92% of the motion is corrected by optical tracking. Because the mechanical performance of the tracking mirror decreases with increased input frequency, tracking performance decreases when the frequency of the motion increases.

Figure 10A:
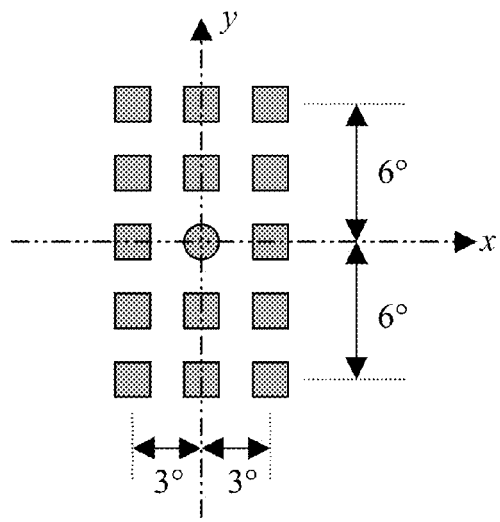
FIGS. 10A-B is an illustration of retinal imaging locations.
Figure 10B:
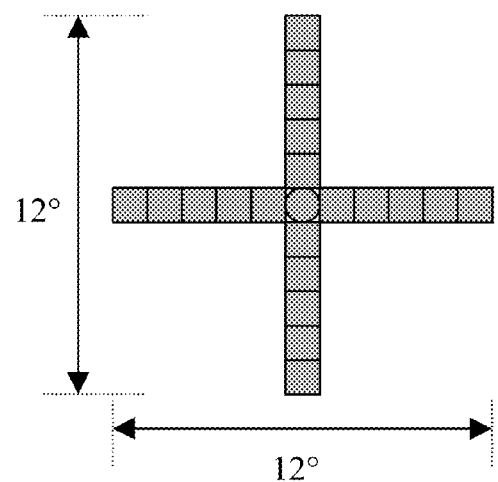

The tracking performance of an embodiment of the ophthalmoscope 400 may also be demonstrated by using a human eye. To test system performance in a living eye, 2-3 image sequences (20 or 30-seconds in duration) were acquired at each of several locations in the central macula. The FOV was ~1.5°×1.5°, or ~434×434 μm on the retina; images were 576×576 pixels. Each image sequence consisted of three stages: 1) no tracking (i.e. normal eye motion), 2) optical stabilization only, and 3) both optical stabilization and digital registration. The frame when each epoch began was recorded digitally for later analysis. Reference frames were selected manually. For three participants (NOR011a, NOR025a, NOR037a), 15 retinal locations were imaged in locations illustrated in FIG. 10A. The fourth participant NOR047a was imaged at 21 retinal locations illustrated in FIG. 10B. The gray circle denotes the foveal center imaging location, while the gray squares denote eccentric imaging locations. The fifth participant NOR046a was imaged at 15 random locations within the central macula. For all participants but NOR046a, retinal locations were targeted using fundus guided fixation target control software; the fixation target, a small white circle (~30 arcminutes in diameter), was projected using an LCD monitor and viewed off of a laser window placed in front of the eye. The fixation target for NOR046a was an array of blue LEDs.

To evaluate system performance, RMS can be calculated separately for each condition using equation (8).

$$RMS = \sqrt{\frac{\sum_{i=1}^{N}(r_i - \bar{r})^2}{N-1}} \quad (8)$$

Where N=F·S, F is the number of frames 960, S is the number of strips 962 in a single frame 960, $r_i$ are the locations of the individual strips, and $\bar{r}$ is the mean location of the strips 962. The RMS values shown in the table below were calculated for all frames 960 successfully tracked with the small amplitude motion component of the algorithm, thus they exclude all spurious motions greater than ½ the strip size, or 16 pixels.

Figure 8:
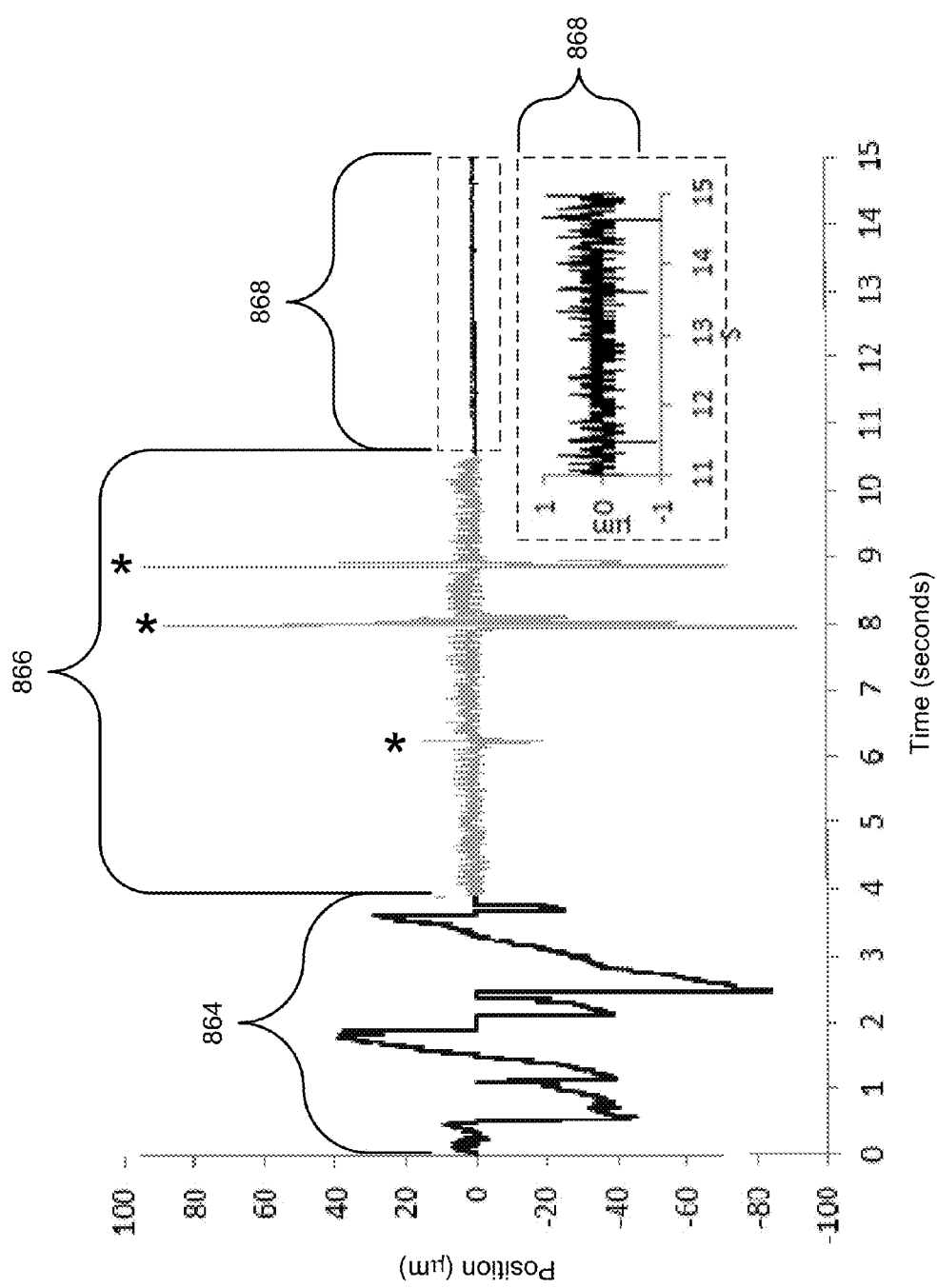
FIG. 8 is an illustration of a motion trace.

A motion trace calculated from a video of a participant is illustrated in FIG. 8. Eye motion 750 without optical stabilization was 26.9 μm RMS in region 864; after optical stabilization it was 2.4 μm RMS in region 866; after both optical stabilization and digital registration it was 0.17 μm RMS in region 868. It should be reiterated that blinks and motion outside the range of the tracking algorithm (i.e. frame out) are not counted in the RMS values reported here, as accurate measurements were outside the current capability of this AOSLO system. In FIG. 8, for example, after optical tracking is turned on, the position values for the three spikes denoted by the asterisks are not counted. This is implemented by adding a second round of cross-correlation, where the stabilized images are correlated with the reference directly with a correlation threshold of 0.85. This step is defined as 'error-proofing' which kicks out all spurious motions from the optically stabilized and digitally registered images. The method has also performed quite well on lower contrast images.

The applicant has found after extensive trials that method using the embodiments described above works almost always. Optical stabilization may fail sometimes if the eye moves too fast at large amplitude (i.e. microsaccades were too frequent) for the operator to manually select a good reference frame. Table 2 lists the performance of optical stabilization for these extensive trials.

Residual RMS ranged from 1.66-2.56 μm 0.34-0.53 arcminutes. Tracking efficiency, defined as the ratio of successfully stabilized frames to the total number of frames after tracking, was 85%, on average, and ranged from 76-92%, depending upon the observer. Tracking efficiency was correlated with the occurrence rate of blinks and microsaccades. The residual RMS after digital registration from all five subjects ranged from ~0.20-0.25 μm or ~0.04-0.05 arcminutes.

Tracking Performance Comparison

The applicants have found that the performance of the embodiments described above is an improvement upon the state of art. Table 3 below describes the present embodiment compares to previous methods. The combination of optical stabilization and digital registration is more accurate than other methods. The performance of optical stabilization alone is comparable only to the optical lever technique (which is impractical for most clinical instruments) and is nearly 10 times better than the optical tracking performance previously reported in AO-SLOs. The combined performance from optical stabilization as used in these embodiments and digital registration is ~3-4 times better than previous methods. Moreover, the successful rate of tracking and tracking efficiency are significantly higher than when suing digital stabilization alone.

TABLE 3

Comparison to other stabilization and registration methods

| Method | Optical stabilization (arcminute) | Digital registration (arcminute) | Description |
| --- | --- | --- | --- |
| Present Embodiments | 0.34-0.53 | 0.04-0.05 | Optical stabilization with digital registration |
| Berkeley AOSLO | N/A | 0.15 | Digital image registration only |
| PSI-IU WF-SLO | 3-4 | N/A | Utilized optic disk reflectometer for optical stabilization |
| Optical lever | 0.2-0.38 | N/A | Direct optical coupling via rigid contact lens |
| dPi eye tracker with an optical deflector | 1 | N/A | Measures displacements of Purkinje reflexes from cornea and lens; coupled to optical deflector |
| EyeRis ™ | 1 | N/A | dPi with gaze contingent display |

Eye Fatigue and Tracking Performance

The applicants found that tracking efficiency may be directly related to imaging duration. Stabilization performance gradually decreased as imaging duration increased. This may be related primarily to decreased tracking efficiency, as there is no apparent relationship with the amount

TABLE 2

Optical stabilization system performance for each participant

| Subject ID | Total Trials | Failed Trials | Tracked Frames | Failed Frames | Tracking Efficiency | Residual RMS (μm) | | |
| --- | --- | --- | --- | --- | --- | --- | --- | --- |
| | | | | | | x | y | r |
| NOR011a | 31 | 0 | 11,357 | 2686 | 76% | 1.86 | 2.76 | 2.04 |
| NOR025a | 39 | 0 | 11,729 | 2039 | 83% | 1.32 | 1.77 | 1.66 |
| NOR037a | 36 | 1 | 14,154 | 2090 | 85% | 1.82 | 2.59 | 2.56 |
| NOR046a | 40 | 0 | 13,585 | 1044 | 92% | 1.44 | 2.04 | 1.87 |
| NOR047a | 37 | 0 | 7,645 | 952 | 88% | 1.38 | 1.95 | 1.68 | of residual motion. Tracking efficiency is directly correlated with the number of frames that can be tracked; we are unable to track blinks and large amplitude motion, such as microsaccades. It may be that this is likely related to increased eye fatigue as microsaccade frequency appears to decrease dramatically after participants take a short break.

Figure 11:
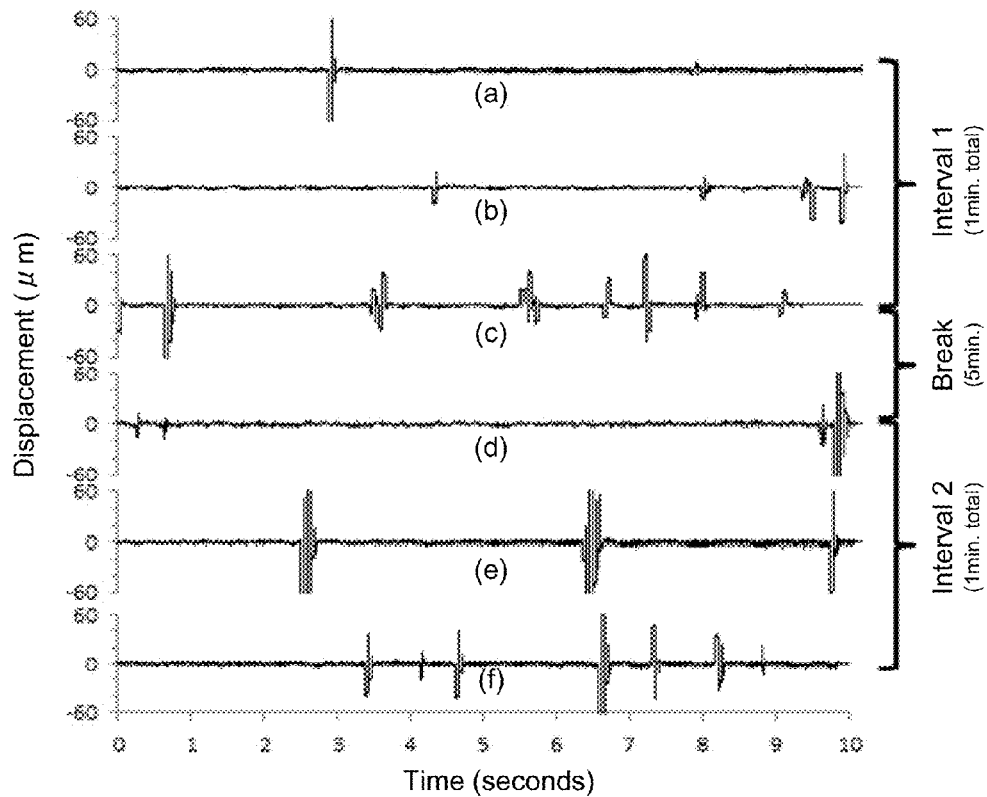
FIG. 11 is an illustration of residual eye motion.

FIG. 11 illustrates representative residual eye motion traces after optical stabilization with elapsing imaging time for subject NOR047A. Each trace corresponds to 10 seconds from a single trial. Asterisks represent spurious motion estimates greater than the limits of the ordinate (i.e. >80 μm). Time intervals between each trace are labeled. 8 trials were recorded from the first 4-minute imaging interval and 7 trials were sampled from the second interval, with a 5 minute break in between. Three trials from each interval are shown here, the first (a, d), middle (b, e) and last (c, f). The tracking efficiencies from traces 1 through 6 are 0.9772→0.9535→0.8762, (5-min break) →0.9539→0.9401→0.9167. The number of large amplitude motion events that could not be tracked (microsaccades, etc.) was greater on the later trials (c, f). Such that the tracking efficiency decreased as the time from the last break increased, and was directly related to the duration from the last break. This further supports the notion that clinical imaging sessions should be kept short and that frequent breaks are required to minimize patient fatigue. Reduced tracking efficiency is likely due to increases in the microsaccade and/or blink rate over time. These events may be a potential sign of patient fatigue and thus indicate when it is time to give a patient a break during a clinical imaging session.

Other Embodiments

An alternative embodiment may include sub-pixel cross-correlation to improve performance by increasing the accuracy of the digital registration. Sub-pixel digital registration to improve performance may be accomplished by spending more computation time on the digital registration or using a higher performance GPU. Increasing registration accuracy increases the $T_5$ latency to ~0.45 ms from ~0.25 ms, and increases the total latency for $T_2$ to $T_5$ from 0.7-0.8 ms to 0.9-1.0 ms. Which within time budget of the feedback to still allow a real-time system to run smoothly.

An alternative embodiment may include real-time error proofing to improve performance by increasing the accuracy of the digital registration. The 'error proofing' step may be implemented in real-time by placing this computation during the period when the scanner runs in reverse direction.

An alternative embodiment may include incorporating automatic reference frame selection to improve performance by speeding up patient viewing, removing some of the operator influence on the results, and reducing operator training requirements. Algorithmic automatic reference frame selection may be used to select a reference frame when there are frequent microsaccades.

An alternative embodiment may include a method for removing intra-frame distortions from the reference frame which may be encoded into the registered images.

An alternative embodiment may include identifying and correcting torsional eye movements (rotations) either optically or digitally.

An alternative embodiment may include faster scanning mirrors. The mechanical performance of the scanning mirrors decreases with increased input frequency, so stabilization performance decreases as the frequency of the motion increases. However, correction of faster eye movements may be achieved by increasing the frame rate of the imaging system; this can be accomplished by either reducing the number of lines per frame or increasing the speed of the resonant scanner. A frame rate for stabilization around 200 Hz could allow for stabilization at the frame rate and would substantially reduce the within frame distortions that are a major problem for clinical imaging used in longitudinal studies of eye disease.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. A method of obtaining an AO (Adaptive Optics) image of an area of a subject, the method comprising:
   providing light from a light source;
   a fast scanning step of scanning the light in a first direction by a first scanner to produce a first scanning line of light;
   a slow scanning step of scanning the first scanning line of light in a second direction by a second scanner, wherein the second direction is substantially orthogonal to the first direction to produce a first scanning area, wherein a scanning rate of the slow scanning step is lower than a scanning rate of the fast scanning step;
   an image constructing step of constructing an image with light from the first scanning area of the subject;
   a position detecting step of detecting a relative change in a position of the first scanning area on the subject by analyzing the image constructed in the image constructing step;
   a tracking step of tracking the first scanning area by controlling the second scanner according to the detected relative change in the position of the first scanning area; and
   an AO image constructing step of constructing the AO image by adjusting a position of the image using the detected relative change in the position of the first scanning area.

2. The method of claim 1, wherein,
   the tracking step further comprises adjusting the second scanner in two orthogonal directions according to the detected relative change in the position of the first scanning area.

3. The method of claim 1, wherein:
   the tracking step comprises controlling an optical tracking system for adjusting the first scanning area in the first scanning direction according to the detected relative change in the position of the first scanning area.

4. The method of claim 1, further comprising:
   obtaining a wide image of the subject that includes the first scanning area of the subject a field of view of the AO image is smaller than a field of view of the wide image; and
   wherein the wide image is used to detect the relative change in the position of the first scanning area as a reference image and the image constructed in the image constructing step is used as a target image.

5. The method of claim 1, wherein,
   analyzing the constructed image includes calculating a cross-correlation between a reference image and a target image to detect the relative change in the position of the first scanning area on the subject.

6. The method of claim 1, wherein,
the relative change in the position of the first scanning area is decomposed into a first relative change in the first direction and a second relative change in the second direction;
the first relative change in the first direction is compensated for by adjusting the position of the image along an axis in the first direction when constructing the AO image; and
the second relative change in the second direction is compensated for by controlling the first scanning area of the second scanner in the second direction according to the second relative change.

7. The method of claim 6, wherein,
the second relative change in the second direction is also compensated for by adjusting the position of the image along an axis in the second direction when constructing the AO image.

8. The method of claim 1, wherein the AO image is one of a video image or an averaged image.

9. The method of claim 1, wherein,
the relative change in the position of the first scanning area is decomposed into a first relative change in the first direction and a second relative change in the second direction; and
the second relative change in the second direction is compensated for by controlling the first scanning area of the second scanner in the second direction according to the second relative change and in the first direction according to the first relative change.

10. An apparatus for obtaining an AO (Adaptive Optics) image of an area of a subject, the apparatus comprising:
a light source providing light;
a first scanner configured to perform a fast scanning step of scanning the light in a first direction to produce a first scanning line of light;
a second scanner configured to perform a slow scanning step of scanning the first scanning line of light in a second direction, wherein the second direction is substantially orthogonal to the first direction to produce a first scanning area, wherein a scanning rate of the slow scanning step is lower than a scanning rate of the fast scanning step;
a processor configured to perform:
an image constructing step of constructing an image with light from the first scanning area of the subject;
a position detecting step of detecting a relative change in a position of the first scanning area on the subject by analyzing the image constructed in the image constructing step;
a tracking step of tracking the first scanning area by controlling the second scanner according to the detected relative change in the position of the first scanning area; and
an AO image constructing step of constructing the AO image by adjusting a position of the image using the detected relative change in the position of the first scanning area.

\* \* \* \* \*